(12) United States Patent
Gibson

(10) Patent No.: US 6,638,945 B1
(45) Date of Patent: Oct. 28, 2003

(54) QUINOLINE DERIVATIVES AS INHIBITORS OF MEK ENZYMES

(75) Inventor: Keith Hopkinson Gibson, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/959,434

(22) PCT Filed: May 3, 2000

(86) PCT No.: PCT/GB00/01698

§ 371 (c)(1),
(2), (4) Date: Oct. 25, 2001

(87) PCT Pub. No.: WO00/68199

PCT Pub. Date: Nov. 16, 2000

(30) Foreign Application Priority Data

May 8, 1999 (GB) .............................. 9910580

(51) Int. Cl.[7] .................. C07D 215/60; C07D 215/38; C07D 215/12; A61K 31/47
(52) U.S. Cl. ..................... 514/311; 514/312; 514/313; 514/314; 546/153; 546/159; 546/176; 546/180
(58) Field of Search ................................ 514/311, 312, 514/313, 314; 546/153, 159, 176, 180

(56) References Cited

U.S. PATENT DOCUMENTS

| | | |
|---|---|---|
| 3,376,195 A | 4/1968 | Allais et al. |
| 3,936,461 A | 2/1976 | Schwender et al. |
| 4,421,920 A | 12/1983 | Baudouin |
| 5,409,930 A | 4/1995 | Spada et al. |
| 5,650,415 A | 7/1997 | Tang et al. |
| 5,656,643 A | 8/1997 | Spada et al. |
| RE36,256 E | 7/1999 | Spada et al. |
| 6,002,008 A | 12/1999 | Wissner et al. |

FOREIGN PATENT DOCUMENTS

| | | |
|---|---|---|
| EP | 0 326 330 | 8/1989 |
| FR | 2 077 455 | 10/1971 |
| WO | 87/04321 | 7/1987 |
| WO | 93/03030 | 2/1993 |
| WO | 96/09294 | 3/1996 |
| WO | 97/03069 | 1/1997 |
| WO | 97/17329 | 5/1997 |
| WO | 98/02434 | 1/1998 |
| WO | 9813350 | * 4/1998 |
| WO | WO 98/43960 | 10/1998 |
| WO | WO 99/01421 | 1/1999 |
| WO | 99/01426 | 1/1999 |
| WO | 99/35146 | 7/1999 |
| WO | 00/18740 | 4/2000 |
| WO | 00/18761 | 4/2000 |

OTHER PUBLICATIONS

Atkins et al., "Synthetic Routes to Quinoline Derivatives: Novel Syntheses of 3–Butyryl–8–methoxy–4–[(2–methylphenyl)amino]quinoline and 3–Butyryl–8–(2– hydroxyethoxy)– 4–[(2–methylphenyl)amino]quinoline", Org. Process Res Dev. vol. 1(3), 1997, pp. 185–197, XP000986311.

Ife et al., Reversible Inhibitors of the Gastric (H[+]/K[+])–ATPase. 3. 3–Substituted–4–(phenylamino)quinolines, J. Med. Chem., 199, 35, pp. 3413–3422, 1992.

Wyszomirski, Conformations of Monosubstituted and Disubstituted 3,4'–, and 3,3'–and 4,4'–Diquinolinyl Sulfides Studied by NMR Spectroscopy, Phosphorus, Sulfur and Silicon, 1994, vol. 95–96, pp. 415–416, Chemical Abstract, 122:264686k, p. 1037, XP–146785, Chemical Abstract, XP–002146786.

* cited by examiner

*Primary Examiner*—D. Margaret Seaman
(74) *Attorney, Agent, or Firm*—Morgan Lewis & Bockius LLP

(57) ABSTRACT

A compound formula (I)

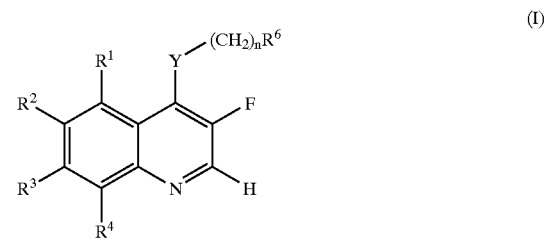

or a pharmaceutically acceptable salt thereof, for use in the manufacture of a medicament for inhibition of MEK in a mammal with a MEK mediated disease wherein: n is 0–1; Y is selected from —NH—, —O—, —S—, or —NR[7]— where R[7] is alkyl of 1–6 carbon atoms R[6] is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be substituted with one, two or three specified substitutents; or R[6] is a group —R[8]—X—R[9] were R[8] is a divalent cycloalkyl of 3 to 7 carbon atoms, which may be optionally further substituted with one or more alkyl of 1 to 6 carbon atom groups; or is an optionally pyridinyl, pyrimidinyl, or phenyl ring; wherein the pyridinyl, pyrimidinyl, or phenyl ring may be optionally further substituted with one or more specified substitutents, X is selected from $CH_2$, —NH—, —O—, —S— or —NR[5]— where R[5] is alkyl of 1–6 carbon atoms, and R[9] is a group $(CH_2)_m R^{10}$ where m is 0, or an integer of from 1–3 and R[10] is an optionally substituted aryl or optionally substituted cycloalkyl ring of up to 10 carbon atoms, or R[10] is a heterocyclic ring containing 1 or 2 oxygen atoms and optionally one or more substitutents; and R[1], R[2], R[3] and R[4] are each independently selected from hydrogen or various specified organic groups. Novel compounds are also described and claimed.

8 Claims, No Drawings

QUINOLINE DERIVATIVES AS INHIBITORS OF MEK ENZYMES

This application is a 371 of PCT/GB00/01698, filed May 3, 2000.

The present invention relates to the use of certain quinoline derivatives in the preparation of medicaments, in particular as inhibitors of specific kinase enzymes, especially MEK enzymes, as well as novel quinoline derivatives. Further aspects of the invention include pharmaceutical compositions and methods of treatment of proliferative disease such as cancer using said compounds.

Cancer is a disease in which cells grow and divide in an uncontrolled fashion. This uncontrolled growth arises from abnormalities in signal transduction pathways that are used by normal cells to regulate cell growth and division in response to various signalling molecules. Normal cells do not proliferate unless stimulated to do so by specific signal molecules located outside the cell derived from nearby cells or tissues. Growth factors bind to the cell membrane via specific receptors which have intrinsic enzyme activity. These receptors relay the growth signal to the cell nucleus via a series of signalling proteins. In cancer, a number of defects in signal pathways are apparent. For example, cancer cells may produce their own growth factors which bind to their cognate receptors, resulting in an autocrine loop, or receptors may be mutated or overexpressed leading to an increased, continuous signal to proliferate. In addition, negative regulators of cell growth may be lost.

Oncogenes are cancer related genes which often encode abnormal versions of signal pathway components, such receptor tyrosine kinases, serine-threonine kinases, or downstream signaling molecules such as the ras genes, which code for closely related small quanine nucleotide binding proteins which hydrolyse bound guanosine triphosphate (GPT) to guanosine diphosphate (GDP). Ras proteins are active in promoting cell growth and transformation when they are bound to GTP and inactive when they are bound to GDP. Transforming mutants of p21ras are defective in their GTPase activity and hence remain in the active GTP bound state. The ras oncogene is known to play an integral role in certain cancers, and has been found to contribute to the formation of over 20% of all cases of human cancer.

When activated by ligand, cell surface receptors which are coupled to the mitogenic response, such as growth factor receptors, initiate a chain of reactions which leads to the activation of guanine nucleotide exchange activity on ras. When in its active GTP-bound state, a number of proteins interact directly with ras at the plasma membrane resulting in signal transmission through several distinct pathways. The best characterised effector protein is the product of the raf proto-oncogene. The interaction of raf and ras is a key regulatory step in the control of cell proliferation. Ras-mediated activation of the raf serine-threonine kinase in turn activates the dual-specificity MEK (MEK1 and MEK2), which is the immediate upstream activator of mitogen activated protein kinase (MAPKs known as extracellular signal regulated protein kinases or ERK1 and ERK2). To date, no substrates of MEK other than MAPK have been identified, though recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

The ras-dependent raf-MEK-MAPK cascade is one of the key signalling pathways responsible for transmitting and amplifying mitogenic signals from cell surface to the nucleus resulting in changes in gene expression and cell fate. This ubiquitous pathway appears essential for normal cell proliferation and constitutive activation of this pathway is sufficient to induce cellular transformation. Transforming mutants of p21ras are constitutively active, resulting in raf, MEK and MAPK activity and cell transformation. Inhibition of MEK activity using either antisense raf, a dominant negative MEK mutant or the selective inhibitor PD098059 have been shown to block the growth and morphological transformation of ras-transformed fibroblasts.

The mechanism of activation of raf, MEK and MAPK is through phosphorylation on specific serine, thronine or tyrosine residues. Activated raf and other kinases phosphorylate MEK1 on S218 and S222 and MEK2 on S222 and S226. This results in MEK activation and subsequent phosphorylation and activation of ERK1 on T190 and Y192 and ERK2 on T183 and Y185 by the dual specificity MEKs. Whilst MEK can be activated by a number of protein kinases, and active MAPKs phosphorylate and activate a number of substrate proteins including transcription factors and other protein kinases, MEKs appear specific and sole activators of MAPKs and could act as a focal point for cross-cascade regulation. MEK1 and MEK2 isoforms show unusual specificity and also contain a proline-rich insert between catalytic subdomains IX and X which is not present in any of the other known MEK family members. These differences between MEK and other protein kinases, together with the known role of MEK in proliferative signalling suggest that it may be possible to discover and employ selective MEK inhibitors as therapeutic agents for use in proliferative disease.

WO 98/43960 discloses a range of 3-cyano quinoline compounds and their use in the treatment of cancer. Certain of the compounds are demonstrated as being inhibitors of Epidermal Growth Factor Receptor Kinase, and to inhibit cancer cell growth. Other quinoline derivatives including fluoro derivatives, which inhibit the effect of growth factors such as VEGF are described in WO98/13350.

This invention provides compounds which are inhibitors of the kinase activity of MEK and as a result, can produce therapeutically useful effects in the treatment of proliferative disease and in particular cancer.

According to the present invention there is provided a compound of formula (I)

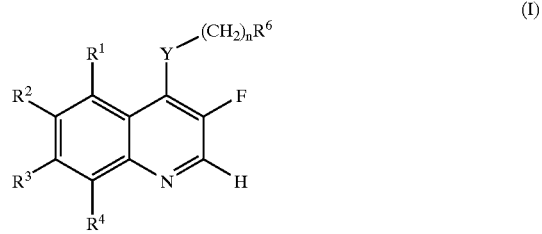

or a pharmaceutically acceptable salt thereof, for use in the manufacture of a medicament for inhibition of MEK in a mammal with a MEK mediated disease wherein:

n is 0–1;

Y is selected from —NH—, —O—, —S—, or —NR$^7$— where R$^7$ is alkyl of 1–6 carbon atoms R$^6$ is cycloalkyl of 3 to 7 carbon atoms, which may be optionally substituted with one or more alkyl of 1 to 6 carbon atom groups; or is a pyridinyl, pyrimidinyl, or phenyl ring;

wherein the pyridinyl, primidinyl, or phenyl ring may be substituted with one, two or three groups selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino;

or $R^6$ is a group $—R^8—X—R^9$ were $R^8$ is a divalent cycloalkyl of 3 to 7 carbon atoms, which may be optionally further substituted with one or more alkyl of 1 to 6 carbon atom groups; or is a divalent pyridinyl, pyrimidinyl, or phenyl ring, wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkyoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from $CH_2$, $—NH—$, $—O—$, $—S—$, or $—NR^5—$ where $R^5$ is alkyl of 1–6 carbon atoms, and $R^9$ is a group $(CH_2)_m R^{10}$ where m is 0, or an integer of from 1–3 and $R^{10}$ is an optionally substituted aryl or optionally substituted cycloalkyl ring of up 10 carbon atoms, or $R^{10}$ is a heterocyclic ring containing 1 to 2 oxygen atoms and optionally one or more substituents;

$R^1$, $R^2$, $R^3$ and $R^4$ are each independently selected from hydrogen, hydroxy, halogeno, cyano, nitro, trifluoromethyl, $C_{1-3}$alkyl, $—NR^{11}R^{12}$ (wherein $R^{11}$ and $R^{12}$, which may be the same or different, each represents hydrogen or $C_{1-3}$alkyl), or a group $R^{13}—X^1—(CH_2)_x$ wherein x is 0 to 3, $X^1$ represents $—O—$, $—CH_2—$, $—OCO—$, carbonyl, $—S—$, $—SO—$, $—SO_2—$, $—NR^{14}CO—$, $—CONR^{15}—$, $—SO_2NR^{16}—$, $—NR^{17}SO_2—$ or $—NR^{18}—$ (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups;

1) $C_{1-5}$alkyl which may be unsubstituted or which may be substituted with one or more groups selected from hydroxy, fluoro and amino;
2) $C_{1-5}$alkyl$X^2COR^{19}$ (wherein $X^2$ represents $—O—$ or $—NR^{20}—$ (wherein $R^{20}$ represents hydrogen, $C_{1-3}$alkyl or $C_{1-3}$alkoxy$C_{2-3}$alkyl) and $R^{19}$ represents $—NR^{21}R^{22}—$ or $—OR^{23}—$ (wherein $R^{21}$, $R^{22}$ and $R^{23}$ which may be the same or different each represents hydrogen, $C_{1-3}$alkyl or $C_{1-3}$alkoxy$C_{2-3}$alkyl));
3) $C_{1-5}$alkyl$X^3R^{24}$ (wherein $X^3$ represents $—O—$, $—S—$, $—SO—$, $—SO_2—$, $—OCO—$, $—NR^{25}CO—$, $—CONR^{26}—$, $—SO_2NR^{27}—$, $—NR^{28}SO_2—$ or $—NR^{29}—$ (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$X^4C_{1-5}$alkyl$X^5R^{30}$ (wherein $X^4$ and $X^5$ which may be the same or different are each $—O—$, $—S—$, $—SO—$, $—SO_2—$, $—NR^{31}CO—$, $—CONR^{32}—$, $—SO_2NR^{33}—$, $—NR^{34}SO_2—$ or $—NR^{35}—$ (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);
5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) $(CH_2)_q X^6 R^{37}$ (wherein q is an integer from 0 to 5, $X^6$ represents a direct bond, $—O—$, $—S—$, $—SO—$, $—SO_2—$, $—NR^{38}CO—$, $—CONR^{39}—$, $—SO_2NR^{40}—$, $—NR^{41}SO_2—$ or $—NR^{42}—$ (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, $—CONR^{43}R^{44}$ and $—NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));
7) $C_{2-6}$alkenyl$R^{36}$ (wherein $R^{36}$ is as defined hereinbefore);
8) $C_{2-6}$alkynyl$R^{36}$ (wherein $R^{36}$ is as defined hereinbefore);
9) $X^7R^{47}$ (wherein $X^7$ is $—SO_2—$, $—O—$ or $—CONR^{48}R^{49}—$ (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is $—SO_2—$, $X^1$ is $—O—$, when $X^7$ is $—O—$, $X^1$ is carbonyl, when $X^7$ is $—CONR^{48}R^{49}—$, $X^1$ is $—O—$ or $NR^{18}$ (wherein $R^{48}$, $R^{49}$ and $R^{18}$ are as defined hereinbefore);
10) $C_{2-6}$alkenyl$R^{37}$ (wherein $R^{37}$ is as defined hereinbefore);
11) $C_{2-6}$alkynyl$R^{37}$ (wherein $R^{37}$ is as defined hereinbefore);
12) $C_{2-6}$alkenyl$X^8R^{37}$ (wherein $X^8$ represents $—O—$, $—S—$, $—SO—$, $—SO_2—$, $—NR^{50}CO—$, $—CONR^{51}—$, $—SO_2NR^{52}—$, $—NR^{53}SO_2—$ or —NR$^{54}$— (wherein R$^{50}$, R$^{51}$, R$^{52}$, R$^{53}$ and R$^{54}$ each independently represents hydrogen, C$_{1-3}$alkyl or C$_{1-3}$alkoxyC$_{2-3}$alkyl) and R$^{37}$ is as defined hereinbefore);

13) C$_{2-6}$alkynylX$^9$R$^{37}$ (wherein X$^9$ represents —O—, —S—, —SO—, —SO$_2$—, —NR$^{55}$CO—, —CONR$^{56}$—, —SO$_2$NR$^{57}$—, —NR$^{58}$SO$_2$— or —NR$^{59}$— (wherein R$^{55}$, R$^{56}$, R$^{57}$, R$^{58}$ and R$^{59}$ each independently represents hydrogen, C$_{1-3}$alkyl or C$_{1-3}$alkoxyC$_{2-3}$alkyl) and R$^{37}$ is as defined hereinbefore);

14) C$_{1-3}$alkylX$^{10}$C$_{1-3}$alkylR$^{37}$ (wherein X$^{10}$ represents —O—, —S—, —SO—, —SO$_2$—, —NR$^{60}$CO—, —CONR$^{61}$—, —SO$_2$NR$^{62}$—, —NR$^{63}$SO$_2$—or —NR$^{64}$— (wherein R$^{60}$, R$^{61}$, R$^{62}$, R$^{63}$ and R$^{64}$ each independently represents hydrogen, C$_{1-3}$alkyl or C$_{1-3}$alkoxyC$_{2-3}$alkyl) and R$^{37}$ is as defined hereinbefore);

15) R$^{36}$ (wherein R$^{36}$ is as defined hereinbefore); and

16) C$_{1-3}$alkylX$^{10}$C$_{1-3}$alkylR$^{36}$ (wherein X$^{10}$ and R$^{36}$ are as defined hereinfore).

In particular, compounds of formula (I) or a pharmaceutically acceptable salt thereof, for use in the manufacture of a medicament for inhibition of MEK in a mammal with a MEK mediated disease are compounds wherein:

n is 0–1;

Y is selected from —NH—, —O—, —S—, or —NR$^7$— where R$^7$ is alkyl of 1–6 carbon atoms R$^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

or R$^6$ is a group —R$^8$—X—R$^9$ where

R$^8$ is a divalent cycloalkyl of 3 to 7 carbon atoms, which may be optionally further substituted with one or more alkyl of 1 to 6 carbon atom groups; or is a divalent pyridinyl, pyrimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from —NH—, —O—, —S—, CH$_2$ or —NR$^5$— where R$^5$ is alkyl of 1–6 carbon atoms, and R$^9$ is a group (CH$_2$)$_m$R$^{10}$ where m is 0, or an integer of from 1–3 and R$^{10}$ is an optionally substituted aryl or optionally substituted cycloalkyl ring of up to 10 carbon atoms, or R$^{10}$ is a heterocyclic ring containing 1 or 2 oxygen atoms and optionally one or more substitutents;

R$^1$, R$^2$, R$^3$ and R$^4$ are each independently selected from hydrogen, hydroxy, halogeno, cyano, nitro, trifluoromethyl, C$_{1-3}$alkyl, —NR$^{11}$R$^{12}$ (wherein R$^{11}$ and R$^{12}$, which may be the same or different, each represents hydrogen or C$_{1-3}$alkyl), or a group R$^{13}$—X$^1$—(CH$_2$)$_x$ wherein x is 0 to 3, X$^1$ represents —O—, —CH$_2$—, —OCO—, carbonyl, —S—, —SO—, —SO$_2$—, —NR$^{14}$CO—, —SO$_2$NR$^{16}$—, —NR$^{17}$SO$_2$— or —NR$^{18}$— (wherein R$^{14}$R$^{16}$, R$^{17}$ and R$^{18}$ each independently represents hydrogen, C$_{1-3}$alkyl or C$_{1-3}$alkoxyC$_{2-3}$alkyl) and R$^{13}$ is selected from one of the sixteen groups listed above.

Certain compounds of formula (I) are novel and these form a further aspect of the invention. In particular, the invention provides a compound of formula (IA) which comprises a compound of formula (I) as defined above, provided that R$^6$ is other than a pyridinyl, pyrimidinyl, or phenyl ring; wherein the pyridinyl, pyrimidinyl, or phenyl ring may be optionally mono- di-, or tri-substituted with a substituent selected from the group consisting of halogen, alkyl of 1–3 carbon atoms, alkoxy of 1–3 carbon atoms, hydroxy, trifluoromethyl, cyano, nitro, amino.

Particular embodiments of compounds of formula (IA) are compounds of formula (I) where n is 0–1;

Y is selected from —NH—, —O—, —S—, or —NR$^7$— where R$^7$ is alkyl of 1–6 carbon atoms R$^6$ is cycloalkyl of 3 to 7 carbon atoms, which may be optionally substituted with one or more alkyl of 1 to 6 carbon atom groups; or is a pyridinyl, pyrimidinyl, or phenyl ring; wherein the pyridinyl, pyrimidinyl, or phenyl ring is substituted with one, two or three groups selected from the group consisting of alkyl of 4–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, carboxy, carboalkoxy of 2–7 carbon atoms, carboalkyl of 2–7 carbon atoms, phenoxy, phenyl, benzoyl, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino;

or R$^6$ is a group —R$^8$—X—R$^9$ where

R$^8$ is a divalent cycloalkyl of 3 to 7 carbon atoms, which may be optionally further substituted with one or more alkyl of 1 to 6 carbon atom groups; or is a divalent pyridinyl, pyrimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

where X is selected from $CH_2$, —NH—, —O—, —S—, $CH_2$ or —$NR^5$— where $R^5$ is alkyl of 1–6 carbon atoms, and $R^9$ is a group $(CH_2)_m R^{10}$ where m is 0, or an integer of from 1–3 and $R^{10}$ is an optionally substituted aryl or optionally substituted cycloalkyl ring of up to 10 carbon atoms, or $R^{10}$ is a heterocyclic ring containing 1 to 2 oxygen atoms and optionally one or more substituents;

$R^1$, $R^2$, $R^3$ and $R^4$ are as defined above.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. A preferred pharmaceutically acceptable salt is a hydrochloride salt.

The alkyl portion of the alkyl, alkoxy, alkanoyloxy, alkoxymethyl, alkanoyloxymethyl, alkylsuphinyl, alkylsulphonyl, alkylsulfonamido, carboalkoxy, carboalkyl, alkanoylamino aminoalkyl, alkylaminoalkyl, N,N-dicycloalkylaminoalkyl, hydroxyalkyl, and alkoxyalkyl substituents include both straight chain as well as branched carbon chains. The cycloalkyl portions of N-cyclalkyl-N-alkylaminoalkyl and N,N-dicycloalkylaminoalkyl substitutents include both simple carbocycles as well as carbocycles containing alkyl substituents. The alkenyl portion of the alkenyl, alkenoyloxymethyl, alkenyloxy, alkenylsulfonamido, substituents include both straight chain as well as branched carbon chains and one or more sites of unsaturation. The alkynyl portion of the alkynyl, alkynoyloxymethyl, alkynylsulfonamido, alkynyloxy, substituents include both straight chain as well as branched carbon chains and one or more sites of unsaturation. Carboxy is defined as a —$CO_2H$ radical. Carboalkoxy of 2–7 carbon atoms is defined as a —$CO_2R"$ radical, where R" is an alkyl radical of 1–6 carbon atoms. Carboalkyl is defined as a —COR" radical, where R" is an alkyl radical of 1–6 carbon atoms. Alkanoyloxy is defined as a —OCR" radical, where R" is an alkyl radical of 1–6 carbon atoms. Alkanoyloxymethyl is defined as $R"CO_2CH_2$— radical, where R" is an alkyl radical of 1–6 carbon atoms. Alkoxymethyl is defined at $R"OCH_2$— radical, where R" is an alkyl radical of –6 carbon atoms. Alkylsulphinyl is defined as R"SO— radical, where R" is an alkyl radical of 1–6 carbon atoms. Alkylsulphonyl is defined as $R"SO_2$, radical, where R" is alkyl radical of 1–6 carbon atoms. Alkylsulfonamido, alkenylsulfonamido, alkynylsulfonamido are defined as $R"SO_2NH$— radical, where R" is an alkyl radical of 1–6 carbon atoms, an alkenyl radical of 2–6 carbon atoms, or an alkynyl radical of 2–6 carbon atoms, respectively. N-alkylcarbamoyl is defined as R"NHCO— radical, where R" is an alkyl radical of 1–6 carbon atoms. N,N-dialkylcarbamoyl is defined as R"R'NCO— radical, where R" is an alkyl radical of 1–6 carbon atoms, R' is an alkyl radical of 1–6 carbon atoms and R', and R" may be the same or different. When X is substituted, it is preferred that it is mono-, di-, or tri-substituted, with monosubstituted being most preferred. It is preferred that of the substituents, $R_1$, $R_2$, $R_3$ and $R_4$ at least one is hydrogen and it is most preferred that two or three be hydrogen. An azacycloalkyl-N-alkyl substituent refers to a monocyclic heterocycle that contains a nitrogen atom on which is substituted a straight or branched chain alkyl radical. A morpholino-N-alkyl substituent is a morpholine ring substituted on the nitrogen atom with a straight or branch chain alkyl radical. A piperidino-N-alkyl substituent is a piperidine ring substituted on one of the nitrogen atoms with a straight or branch chain alkyl radical. A N-alkyl-piperazino-N-alkyl substituent is a piperazine ring substituted on one of the nitrogen atoms with a straight or branched chain alkyl group and on the other nitrogen atom with a straight or branch chain alkyl radical.

When any group contains an alkyl portion, the alkyl portion contains preferably 1–6 carbon atoms, more preferably 1–4 carbon atoms, particularly methyl, ethyl, n-propyl, iso-propyl, n-butyl, iso-butyl, sec-butyl, sec-butyl or tert-butyl. When any group contains an alkenyl or alkynyl portion, the alkenyl or alkynyl portion contains preferably 2–6 carbon atoms, more preferably 2–4 carbon atoms.

The term "aryl" used herein includes aromatic carbocyclic compounds, for example of from 6 to 20 atoms such as phenyl or naphthyl. The term "heterocyclic" refers to ring structures suitably from 5 to 20 atoms in size, up to four of which are heteroatoms such as oxygen, sulphur and nitrogen. The ring structures may be monocyclic, bi- or tricyclic and be aromatic or non-aromatic in character including the possibility that part of a ring system has aromatic character whilst other parts do not.

The compounds of this invention may contain an asymmetric carbon; in such cases, the compounds of this invention cover the racemate and the individual R and S entantiomers, and in the case were more than one asymmetric carbon exists, the individual diasteromers, their racemates and individual entantiomers.

Suitable examples of groups Y are —NH—.

In a preferred embodiment, the group $R^6$ is a group —$R^8$—X—$R^9$ where $R^8$, X and $R^9$ are as defined above. Suitably X is oxygen.

Preferably n is 0.

Examples of optional substituents for groups $R^{10}$ include one or more groups selected from hydroxy, halo; nitro; cyano; carboxy; $C_{1-6}$alkoxy; $C_{1-6}$alkyl; $C_{2-6}$alkenyl ; $C_{2-6}$alkynyl; $C_{2-6}$alkenyloxy; $C_{2-6}$alkynyloxy; $C_{3-6}$cycloalkyl; amino; mono- or di-$C_{1-6}$alkyl amino; heterocyclyl optionally substituted with $C_{1-6}$alkyl or oxo; C(O)$R^a$; C(O)O$R^a$; S(O)$_d R^a$; N$R^a$C(O)$R^b$; C(O)N$R^a$S(O)$_d R^b$; C(O)N$R^a R^b$; N$R^a$C(O)N$R^b R^c$; N$R^a$S(O)$_d R^b$ or N(S(O)$_d R^b$)S(O)$_d R^c$ where d is 0, 1 or 2 and $R^a$, $R^b$ and $R^c$ are independently selected from hydrogen, $C_{1-6}$alkyl, aryl, $C_{3-6}$cycloalkyl or heterocyclyl, and wherein any alkyl, alkenyl or alkynyl group or moiety contained within the substituent $R^{10}$ may themselves be optionally substituted with one or more groups selected from hydroxy; cyano; nitro; halo; carboxy; carboalkoxy of 2–7 carbon atoms; $C_{3-6}$cycloalkyl; heterocyclyl optionally substituted with $C_{1-6}$alkyl or oxo; C(O)$R^d$; C(O)O$R^d$; N$R^d R^e$; S(O)$_e R^d$; N$R^d$C(O)$R^e$; C(O)N$R^d R^e$; N$R^d$C(O)N$R^e R^f$; N$R^d$S(O)$_e R^e$ where e is 0, 1 or 2 and $R^d$, $R^e$ and $R^f$ are independently selected from hydrogen or $C_{1-6}$alkyl optionally substituted with one or more groups selected from hydroxy; cyano; nitro; halo; carboxy; carboalkoxy of 2–7 carbon atoms; $C_{3-6}$cycloalkyl; heterocyclyl optionally substituted with $C_{1-6}$alkyl or oxo; C(O)$R^g$; C(O)O$R^g$; N$R^g R^h$; S(O)$_e R^g$; N$R^h$C(O)$R^g$; C(O)N$R^g R^h$; N$R^g$C(O)N$R^h R^i$; N$R^g$S(O)$_e R^h$ where e is as defined above and $R^g$, $R^h$ and $R^i$ are independently selected from hydrogen or $C_{1-6}$alkyl. Alternatively, two substituents on adjacent atoms may be joined to form the second ring of a bicyclic ring system wherein the said second ring is optionally substituted with one or more of the groups listed above for $R^{10}$ and optionally contains one or more heteroatoms.

In some embodiments, the level of substitution on the group $R^{10}$ is a chain substituted with complex substituents. Thus, for example, a substituent may comprise an substituted alkyl chain which is optionally interposed with heteroatoms such as groups of sub-formula (i)

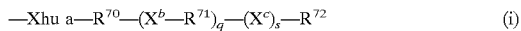

where $X^a$, $X^b$ and $X^c$ are independently selected from any of the groups listed above for $X^1$, $R^{70}$ and $R^{71}$ are independently selected from $C_{1-4}$alkylene, $C_{2-4}$alkenylene or $C_{2-4}$alkynylene groups any of which may be optionally substituted with hydroxy; cyano; nitro; halo; carboxy, carboalkyoxy of 2–7 carbon atoms or $C_{3-4}$cycloalkyl;

$R^{72}$ is hydrogen or an $C_{1-4}$alkyl, $C_{2-4}$ alkenyl or $C_{2-4}$alkynyl group any of which may be optionally substituted with hydroxy; cyano; nitro; halo; carboxy or $C_{3-4}$cycloalkyl;

and q and s are independently 0 to 1.

Particular examples of substituents for $R^{10}$ include halo such as fluoro and chloro, $G_{1-6}$ alkylamino, cyano, carboxy, carboalkoxy of 2 to 7 carbon atoms, or alkoxy such as methoxy, optionally substituted, in particular by $C(O)NR^aR^b$ were $R^a$ and $R^b$ are as defined above.

Preferably $R^{10}$ is an aryl group substituted by an optionally substituted alkoxy group and most preferably, $R^{10}$ is an aryl group substituted by a substituted alkoxy group.

Preferably n is 0.

Particular examples of groups $R^{10}$ include phenyl or cyclalkyl of from 3–8 and preferably of 6 carbon atoms which are substituted at the ortho or meta position and preferably at the ortho position. Particularly preferred substituents are an alkoxy groups, in particular methoxy.

When $R^{10}$ is substituted phenyl or cycloalkyl, m is preferably 0.

Examples of heterocyclic rings $R^{10}$ include 3–7 membered rings, up to two of which may be oxygen atoms. Such groups include:

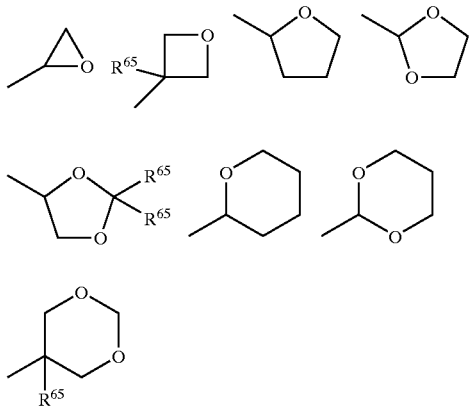

where each $R^{65}$ is independently selected from hydroxy or $C_{1-6}$alkyl and especially methyl. In such compounds, m is suitably 1, 2 or 3.

Other examples of heterocyclic groups $R^{10}$ include pyridyl, thiazolyl, pyrazinyl, pyrimidinyl, oxadiazole, and in particular is thiazolyl.

Suitable further substitutents for $R^8$ include those listed above for pyridyl, pyrimidinyl and phenyl groups $R^6$.

Thus a preferred sub-group of compounds of formula (I) are compounds of formula (II)

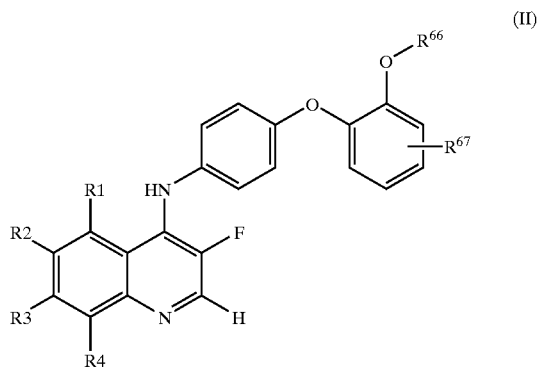

where $R^1$, $R^2$, $R^3$ and $R^4$ are as defined above and $R^{66}$ is $C_{1-6}$ alkyl in particular methyl and $R^{67}$ is selected from hydrogen, halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino.

Preferably $R^{67}$ is hydrogen.

Examples of preferred groups for $R^1$, $R^2$, $R^3$ and $R^4$ are set out in WO 98/13350.

Preferably x is 0. Conveniently $R^{13}$ is selected from one of the following sixteen groups:

1) $C_{1-5}$alkyl which may be unsubstituted or substituted with one or more fluorine atoms, or $C_{2-5}$alkyl which may be unsubstituted or substituted with one or more groups selected from hydroxy and amino;

2) $C_{2-3}$alkylX$^2$COR$^{19}$ (wherein $X^2$ is as defined hereinbefore and $R^{19}$ represents —NR$^{21}$R$^{22}$— or —OR$^{23}$— (wherein $R^{21}$, $R^{22}$ and $R^{23}$ which may be the same or different each represents hydrogen, $C_{1-2}$alkyl or $C_{1-2}$alkoxyethyl));

3) $C_{2-4}$alkylX$^3$R$^{24}$ (wherein $X^3$ is as defined hereinbefore and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-3}$alkoxy and which cyclic group may bear one or two substituents selected from oxo, hydroxy, halogeno, $C_{1-3}$alkyl, $C_{1-3}$hydroxyalkyl and $C_{1-3}$alkoxy);

4) $C_{2-3}$alkylX$^4$C$_{2-3}$alkyl X$^5$R$^{30}$ (wherein $X^4$ and $X^5$ are as defined hereinbefore and $R^{30}$ represents hydrogen or $C_{1-3}$alkyl);

5) $C_{1-5}$alkyl R$^{70}$ (wherein $R^{70}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-3}$alkyl, $C_{1-3}$hydroxyalkyl and $C_{1-3}$alkoxy) or $C_{2-5}$alkylR$^{71}$ (wherein R$^{71}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-3}$alkyl, $C_{1-3}$hydroxyalkyl and $C_{1-3}$alkoxy);

6) $(CH_2)_q X^6 R^{37}$ (wherein X$^6$ is as defined hereinbefore; q is an integer from 0 to 4 if X$^6$ is a direct bond and q is 0, 2 or 3 if X$^6$ is other than a direct bond; and R$^{37}$ is a phenyl group, a pyridone group or a 5 or 6 membered aromatic heterocyclic group with 1 to 3 heteroatoms selected from O, N and S, of which preferably one is N, which phenyl group, pyridone group or aromatic heterocyclic group may be substituted as hereinbefore defined, advantageously substituted with up to 2 substituents as hereinbefore defined, more preferably substituted with one substituent selected from the group of substituents as hereinbefore defined);

7) $C_{4-5}$alkenylR$^{72}$ (wherein R$^{72}$ represents R$^{70}$ or R$^{71}$ as defined hereinbefore);

8) $C_{4-5}$alkynylR$^{72}$ (wherein R$^{72}$ represents R$^{70}$ R$^{71}$ as defined hereinbefore);

9) X$^7$R$^{47}$ (wherein X$^7$ is as defined hereinbefore and R$^{47}$ represents $C_{1-3}$alkyl which may be unsubstituted or which may be substituted with one or more groups selected from hydroxy, fluoro and amino);

10) $C_{3-5}$alkenylR$^{37}$ (wherein R$^{37}$ is as defined hereinbefore);

11) $C_{3-5}$alkynylR$^{37}$ (wherein R$^{37}$ is as defined hereinbefore);

12) $C_{4-5}$alkenylX$^8$R$^{37}$ (wherein X$^8$ and R$^{37}$ are as defined hereinbefore);

13) $C_{4-5}$alkynylX$^9$R$^{30}$ (wherein X$^9$ and R$^{30}$ are as defined hereinbefore);

14) $C_{1-3}$alkylX$^{10}$C$_{1-3}$alkylR$^{37}$ (wherein X$^{10}$ and R$^{37}$ are as defined hereinbefore);

15) R$^{36}$ (wherein R$^{36}$ is as defined hereinbefore); and

16) $C_{1-3}$alkylX$^{11}$C$_{1-3}$alkylR$^{36}$ (wherein X$^{11}$ and R$^{36}$ are as defined hereinbefore).

Advantageously R$^{13}$ is selected from one of the following eleven groups:

1) $C_{1-4}$alkyl which may be unsubstituted or substituted with one or more fluorine atoms, or $C_{2-4}$alkyl which may be unsubstituted or substituted with one or two groups selected from hydroxy and amino;

2) $C_{2-3}$alkylX$^2$COR$^{19}$ (wherein X$^2$ is as defined hereinbefore and R$^{19}$ represents —NR$^{21}$R$^{22}$— or —OR$^{23}$— (wherein R$^{21}$, R$^{22}$ and R$^{23}$ which may be the same or different each represents hydrogen, $C_{1-2}$alkyl or $C_{1-2}$alkoxyethyl));

3) $C_{2-3}$alkylX$^3$ R$^{24}$ (wherein X$^3$ is as defined hereinbefore and R$^{24}$ is a group selected from $C_{1-3}$alkyl, cyclopentyl, cyclohexyl, pyrrolidinyl and piperidinyl which group is linked to X$^3$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkylX$^4$C$_{2-3}$alkylX$^5$R$^{30}$ (wherein X$^4$ and X$^5$ are as defined hereinbefore) and R$^{30}$ represents hydrogen or $C_{1-2}$alkyl);

5) $C_{1-4}$alkylR$^{70}$ (wherein R$^{70}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$-alkyl, $C_{1-2}$hydroxyalkyl and $C_{1-2}$alkoxy) or $C_{2-4}$alkylR$^{71}$ (wherein R$^{71}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy); and 6) $(CH_2)_q X^6 R^{37}$ (wherein X$^6$ is as defined hereinbefore; q is an integer from 1 to 3 if X$^6$ is a direct bond and q is 2 or 3 if X$^6$ is other than a direct bond; and R$^{37}$ is a phenyl group, a pyridone group or a 5 or 6 membered aromatic heterocyclic group with 1 to 2 heteroatoms selected from O, N and S, of which preferably one is N, which phenyl group, pyridone group or aromatic heterocyclic group may be substituted as hereinbefore defined, preferably substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —CONR$^{43}$R$^{44}$ and —NR$^{45}$COR$^{46}$ (wherein R$^{43}$, R$^{44}$, R$^{45}$ and R$^{46}$, which may be the same or different, each represents hydrogen or $C_{1-2}$alkyl));

7) $C_{4-5}$alkenylR$^{71}$ (wherein R$^{71}$ is as defined hereinbefore);

8) $C_{4-5}$alkynylR$^{71}$ (wherein R$^{71}$ is as defined hereinbefore);

9) $C_{1-3}$alkylX$^{10}$C$_{1-3}$alkylR$^{37}$ (wherein X$^{10}$ and R$^{37}$ are as defined hereinbefore);

10) R$^{36}$ (wherein R$^{36}$ is as defined hereinbefore); and

11) $C_{1-3}$alkylX$^{11}$C$_{1-3}$alkylR$^{36}$ (wherein X$^{11}$ and R$^{36}$ are as defined hereinbefore).

Preferably R$^{13}$ is selected from one of the following nine groups:

1) $C_{1-3}$alkyl which may be unsubstituted or substituted with one or more fluorine atoms, or $C_{2-3}$alkyl which may be unsubstituted or substituted with one or more groups selected from hydroxy and amino;

2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkylX$^3$R$^{24}$ (wherein X$^3$ is as defined hereinbefore and R$^{24}$ is a group selected from $C_{1-2}$alkyl, cyclopentyl, cyclohexyl, pyrrolidinyl and piperidinyl which group is linked to X$^3$ through a carbon atom and which $C_{1-2}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{32}$ (wherein $X^4$ and $X^5$ are as defined hereinbefore) and $R^{30}$ represents hydrogen or $C_{1-2}$alkyl);

5) $C_{1-2}$alkyl$R^{70}$ (wherein $R^{70}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{59}$ (wherein $R^{59}$ is a group selected from morpholino, thiomorpholino, piperidino, piperazin-1-yl and pyrrolidin-1-yl which group may carry one or two substituents selected from oxo, hydroxy, halogeno, $C_{1-2}$alkyl, $C_{1-2}$hydroxyalkyl and $C_{1-2}$alkoxy);

6) $(CH_2)_qX^6R^{37}$ (wherein $X^6$ is as defined hereinbefore; q is an integer from 1 to 3 if $X^6$ is a direct bond and q is 2 or 3 if $X^6$ is other than a direct bond; and $R^{37}$ is a group selected from phenyl, a pyridone group, pyridyl, imidazolyl, thiazolyl, thienyl, triazolyl and pyridazinyl, preferably selected from phenyl, a pyridone group, pyridyl, imidazolyl, thiazolyl and triazolyl which group may be substituted with one substituent selected from hydroxy, halogeno, $C_{1-2}$alkyl, $C_{1-2}$alkoxy, $C_{1-2}$hydroxyalkyl, $C_{1-2}$hydroxyalkoxy, carboxy, cyano, —$CONR^{43}R^{44}$ and —$NR^{45}COR^{46}$ (wherein $R^{43}$, $R^{44}$, $R^{45}$ and $R^{46}$ are as defined hereinbefore);

7) $C_{1-3}$alkyl$X^{10}C_{1-3}$alkyl$R^{37}$ (wherein $X^{10}$ and $R^{37}$ are as defined hereinbefore);

8) $R^{36}$ (wherein $R^{36}$ is as defined hereinbefore); and

9) $C_{1-3}$alkyl$X^{11}C_{1-3}$alkyl$R^{36}$ (wherein $X^{11}$ and $R^{36}$ are as defined hereinbefore).

More preferably $R^{13}$ represents 2-methylthio-4-yl methyl, 2-acetamido-4-ylmethyl, 1-methylimidazol-2-ylmethyl, 4-pyridylmethyl, 2-(4-pyridyl)ethyl, 3-(4-pyridyl)propyl, 2-((N-(1-methylimidazol-4-ylsulphonyl)-N-methyl)amino) ethyl, 2-((N-(3-morpholinopropylsulphonyl)-N-methyl) amino)ethyl, 2((N-methyl-N-4-pyridyl)amino)ethyl, 2-(4-oxidomorpholino)ethyl, 3-(4-oxidomorpholino)propyl, 2-(4-oxo-1,4-dihydro-1-pyridyl)ethyl, 3-(4-oxo-1,4-dihydro-1-pyridyl)propyl, methyl, ethyl, trifluoromethyl, 2,2,2-trifluoroethyl, 2-hydroxyethyl, 3-hydroxypropyl, 2-(N,N-dimethylsulphamoyl)ethyl, 2-(N-methylsulphamoyl)ethyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-(1,2,4-triazol-1-yl)ethyl, 2-(1,2,4 triazol-4-yl)ethyl, 3-(1,2,4-triazol-1-yl)propyl, 3-(1,2,4-triazol-4-yl)propyl, 2-(4-pyridyloxy)ethyl, 3-(4-pyridyloxy)propyl, 2-(4-pyridylamino)ethyl, 3-(4-pyridylamino)propyl, 2-(2-methylimidazol-1-yl)ethyl, 3-(2-methylimidazol-1-yl)propyl, 2-(5-methyl-1,2,4-triazol-1-yl) ethyl, 3-(5-methyl-1,2,4-triazol-1-yl)propyl, morpholino, N-methylpiperazinyl, piperazinyl, 2-(N,N-dimethylamino) ethyl, 3-N,N-dimethylamino)propyl, 2-morpholinoethyl, 3-piperazin-1-yl)propyl, 2-pyrrolidin-1-yl)ethyl, 3-(pyrrolidin-1-yl)ethyl, 2-(1,2,3-triazol-2-yl)ethyl, 3-(imidazol-1-yl)propyl, 3-(1,2,3-triazol-1-yl)propyl, 3-(1,2,3-triazol-2-yl)propyl, 2-thiomorpholinoethyl, 3-thiomorpholinopropyl, 2-(1,1-dioxothiomorpholino)ethyl, 3-(1,1-dioxothiomorpholino)propyl, 2-(2-methoxyethoxy) ethyl, 2-(4-methylpiperazin-1-yl)ethyl, 3-(4-methylpiperazin-1-yl)propyl, 3-methylsulphinyl)propyl, 3-(methylsulphonyl)propyl, 2-(methylsulphinyl)ethyl, benzyl, 2-sulphamoylethyl or 2-(methylsulphonyl)ethyl.

Especially $R^{13}$ represents methyl, ethyl, trifluoromethyl, 2,2,2-trifluoroethyl, 2-hydroxyethyl, 3-hydroxypropyl, 2-methoxyethyl, 3-methoxypropyl, 2-methylsulphinyl) ethyl, 2-(methylsulphonyl)ethyl, 2-(N,N-dimethylsulphamoyl)ethyl, 2-(N-methylsulphamoyl)ethyl, 2-sulphamoylethyl, 2(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl) ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 3-(3-pyridyl)propyl, benzyl, 2-(4-pyridyloxy)ethyl, 2-(4-pyridylamino)ethyl, or 2-(4-oxo-1,4-dihydro-1-pyridyl) ethyl.

More especially $R^{13}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl) ethyl, 2-sulphamoylethyl, 2-(N,N-dimethylamino)ethyl, 3(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 2-acetamidothiazol-4-ylmethyl, 1-methylimidazol-2-ylmethyl, 2-(imidazol-1-yl) ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, benzyl, 2-(4-pyridyloxy)ethyl, 2-(4-pyridylamino)ethyl, or 2-(4-oxo-1,4-dihydro-1-pyridyl)ethyl.

In particular $R^1$ and $R^4$ are suitably hydrogen.

Examples of preferred groups for $R^2$ include $C_{1-6}$alkoxy.

The group $R^3$ is suitably selected from hydrogen or $C_{1-6}$alkoxy.

Preferably both $R^2$ and $R^3$ are $C_{1-6}$alkoxy and are preferably methoxy.

A further preferred group for $R^2$ or $R^3$ is 3-morpholinopropyloxy.

Particular examples of compounds of formula (I) are listed in Table 1.

TABLE 1
| NO. | R¹ | R² | R³ | R⁴ | R⁶ | Y | n |
|---|---|---|---|---|---|---|---|
| 1 | H | OCH₃ | OCH₃ | H | 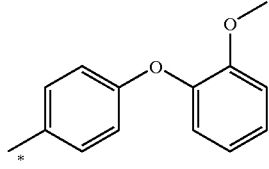 | NH | 0 |
| 2 | H | OCH₃ | OCH₃ | H | 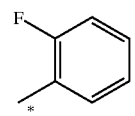 | NH | 0 |
| 3 | H | OCH₃ | OCH₃ | H | 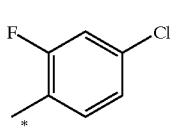 | NH | 0 |
| 4 | H | OCH₃ | OCH₃ | H | 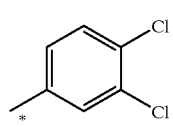 | NH | 0 |
| 5 | H | OCH₃ | OCH₃ | H | 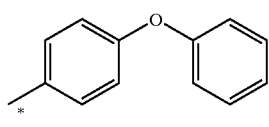 | NH | 0 |
| 6 | H | OCH₃ | OCH₃ | H | 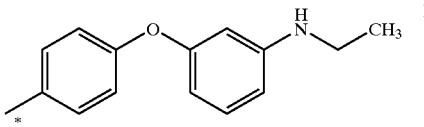 | NH | 0 |
| 7 | H | OCH₃ | OCH₃ | H | 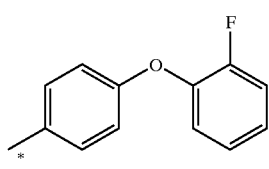 | NH | 0 |
| 8 | H | OCH₃ | OCH₃ | H | 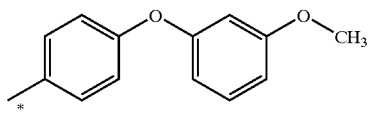 | NH | 0 |
| 9 | H | OCH₃ | OCH₃ | H | 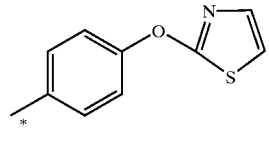 | NH | 0 |
| 10 | H | OCH₃ | OCH₃ | H | 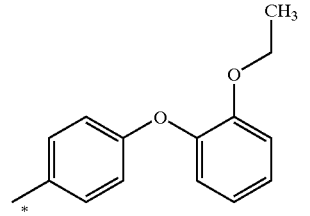 | NH | 0 |

TABLE 1-continued

| NO. | R¹ | R² | R³ | R⁴ | R⁶ | Y | n |
|-----|----|----|----|----|----|---|---|
| 11 | H | OCH₃ | OCH₃ | H | (4-methylphenoxy)-2-(N-methylcarbamoylmethoxy)phenyl | NH | 0 |
| 12 | H | OCH₃ | OCH₃ | H | 2-(4-methylphenoxy)phenyl methyl carboxylate | NH | 0 |
| 13 | H | OCH₃ | OCH₃ | H | 4-(pyridin-2-yloxy)phenyl | NH | 0 |
| 14 | H | OCH₃ | OCH₃ | H | 4-(2-cyanophenoxy)phenyl | NH | 0 |
| 15 | H | OCH₃ | OCH₃ | H | 4-benzylphenyl | NH | 0 |
| 16 | H | OCH₃ | OCH₃ | H | 4-methyl-3-methyl-(2-cyanophenoxy)phenyl | NH | 0 |
| 17 | H | OCH₃ | OCH₃ | H | 5-(2-methoxyphenoxy)pyridin-2-yl | NH | 0 |
| 18 | H | OCH₃ | OCH₃ | H | 4-(3-cyanophenoxy)phenyl | NH | 0 | where * indicates the point of attachment.

Compounds of formula (I) are suitably prepared by reacting a compound of formula (III)

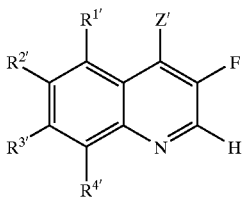

(III)

where $R^{1'}$, $R^{2'}$, $R^{3'}$, $R^{4'}$ represent $R^1$, $R^2$, $R^3$ and $R^4$ respectively as defined in relation to formula (I) or a precursor thereof, and Z' is a leaving group, with a compound of formula (IV)

(IV)

where Y, X, and n are as defined in relation to formula (I), and $R^{6'}$ is a group $R^6$ as defined in relation to formula (I) or a precursor thereof; and thereafter if necessary or desired converting precursor groups $R^{1'}$, $R^{2'}$, $R^{3'}$, $R^{4'}$ and $R^{6'}$ to groups of formula $R^1$, $R^2 R^3$, $R^4$ and $R^6$ respectively, or converting a group $R^1$, $R^2$, $R^3$, $R^4$ and $R^6$ to a different such group.

Suitable leaving groups for Z' include halogen such as bromo or chloro, or a mesylate or tosylate group. In particular Z' is chloro.

The reaction is suitably carried out in an organic solvent such as an alcohol for example propanol, cyclohexanol, at elevated temperatures, for example of from 50 to 150° C., for example at about 105° C. or 110° C.

Conversion reactions in which precursor groups $R^{1'}$, $R^{2'}$, $R^{3'}$, $R^{4'}$ are converted to groups of formula $R^1$, $R^2$, $R^3$ and $R^4$ respectively, or groups $R^1$, $R^2$, $R^3$ and $R^4$ are converted to different such group can be carried out using conventional chemistry as described in the literature. Particular precursor groups $R^{1'}$, $R^{2'}$, $R^{3'}$, $R^{4'}$ are groups of formula $R^{13'}$—$X^1$—$(CH_2)_x$ wherein x and $X^1$ are as defined hereinafter, and $R^{13'}$ is $C_{1-5}$alkyl which is substituted with halo other than fluoro, and in particular chloro or bromo. The chloro group may readily be converted many other groups $R^{13}$ as defined in relation to claim 1. Such compounds are novel and form a further aspect of the invention. They may have activity similar to that of compounds of formula (I) in their own right and therefore may be used in place of a compound of formula (I).

Thus the invention further provides a compound of formula (IB)

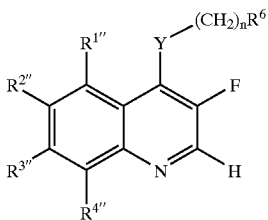

(IB)

where Y, n and $R^6$ are as defined above and at least one of $R^{1''}$, $R^{2''}$, $R^{3''}$ or $R^{4''}$ is a group $R^{13'}$—$X^1$—$(CH_2)_x$ wherein $X^1$ and x are as above and $R^{13'}$ is alkyl substituted by chloro or bromo; and the remainder are groups $R^1$, $R^2$, $R^3$ and $R^4$ respectively.

Similarly conversion reactions involving groups $R^{6'}$ may be effected using conventional chemistry. For example substituent groups on a group $R^6$ may be changed, for example by changing acids to esters or amides etc.

A further method for producing compounds of formula (I) where $R^6$ is a group —$R^8$—X—$R^9$ is to react a compound of formula (V)

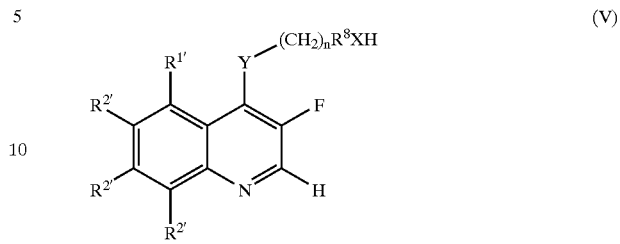

(V)

where $R^{1'}$, $R^{2'}$, $R^{3'}$, $R^{4'}$ are as defined in relation to formula (III) $R^8$, X, Y and n are as defined in relation to formula (I), with a compound of formula (VI)

(VI)

where $R^{9'}$ is a group $R^9$ as defined in relation to formula (IV) or a precursor thereof and Z'' is a leaving group; and thereafter if necessary or desired converting precursor groups $R^{1'}$, $R^{2'}$, $R^{3'}$, $R^{4'}$ and $R^{9'}$ to groups of formula $R^1$, $R^2$, $R^3$, $R^4$ and $R^9$ respectively, or converting a group $R^1$, $R^2$, $R^3$, $R^4$ and $R^9$ to a different such group. Suitable leaving groups for Z'' include halogen such as bromo or chloro, or a mesylate or tosylate group. Conversion reactions are as described above.

The reaction is suitably carried out in an organic solvent such as DMF at elevated temperatures, for example of from 40 to 120° C., for example at about 80° C.

Preferably however, $R^{1'}$, $R^{2'}$, $R^{3'}$, $R^{4'}$, and $R^{6'}$ are groups $R^1$, $R^2$, $R^3$, $R^4$ and $R^6$ respectively and so no subsequent processing is required.

Compounds of formula (IV) are known compounds (see for example Rev. Chim. (Bucharest) (1988), 39(6), 477–82 and DD 110651: 74.01.05) or they can be prepared from known compounds using conventional methods. Compounds of formula (VI) are also known compounds or they can be prepared from known compounds by conventional methods.

Certain compounds of formula (III) are disclosed in WO98/13350 and others can be prepared from known compounds by analogous methods. For example, they are suitably prepared by reacting a compound of formula (V)

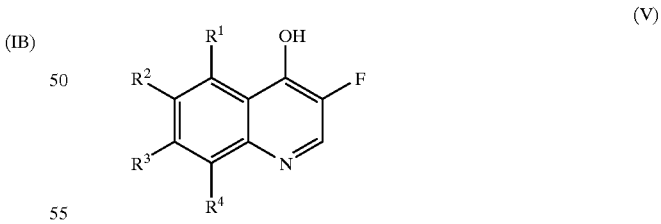

(V)

where $R^1$, $R^2$, $R^3$ and $R^4$ are as defined in relation to formula (I), with a compound of formula (VI)

(VI)

where Z' is as defined above and $R^{67}$ is a further leaving group such as sulphonylchloride. A particular example of a compound of formula (VI) is thionyl chloride.

The reaction is suitably effected in an organic solvent such as dimethylformamide, at elevated temperatures for example of from 50 to 150° C., and conveniently at the reflux temperature of the solvent.

Compounds of formula (V) may be prepared from known compounds by conventional methods such as those described in WO 98/13350. Compounds of formula (IV) are also either known compounds (see for example Rev. Chim. (Bucharest (1988), 39(6), 477–82, DD110651: 74.01.05) or they can be prepared from known compounds by conventional methods.

Altenatively compounds of formula (III) may be prepared by heating a tetraborofluoroate salt of formula (VII)

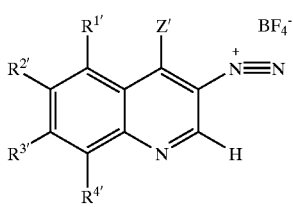

(VII)

where $R^{1'}$, $R^{21}$, $R^{3'}$ $R^{4'}$ and $Z'$ are as defined in relation to formula (III). Suitable temperatures will be of the order of 150 to 200° C. and preferably at about 170° C.

Compounds of formula (VII) are suitably prepared by reacting a compound of formula (VIII)

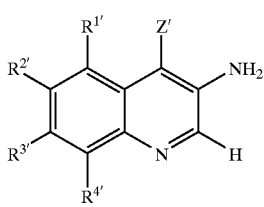

(VIII)

where $R^{1'}$, $R^{21}$, $R^{3'}$ $R^{4'}$ and $Z'$ are as defined in relation to formula (III); with fluoroboric acid in the presence of a nitrite salt such as an alkali metal nitrite like sodium nitrile. The reaction is suitably effected in an organic solvent such as tetrahydrofuran. Suitable temperatures are low temperatures of from –10° C. to 15° C. and preferably at about 10° C.

Compounds of formula (VIII) in turn may be obtained by hydrolysis and decarboxylation of compounds of formula (IX)

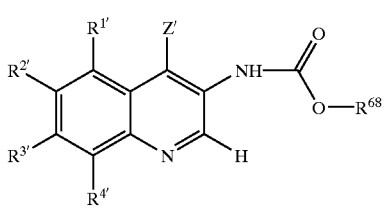

(IX)

where $R^{68}$ is an alkyl group such as t-butyl, and $R^{1'}$, $R^{21}$, $R^{3'}$ $R^{4'}$ and $Z'$ are as defined in relation to formula (III). The reaction is suitably effected by an organic acid such as TFA in the presence of a scavenging agent such as triethylsilane. A base such as ammonia can then be used to generate the free base of formula (VIII). Moderate temperatures, conveniently ambient temperatures are employed.

Compounds of formula (IX) maybe prepared by reacting a compound of formula (X)

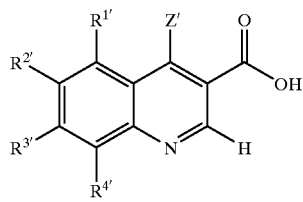

(X)

where $R^{1'}$, $R^{21}$, $R^{3'}$ $R^{4'}$ and $Z'$ are as defined in relation to formula (III) with a compound of formula (XI)

$$R^{68}-OH$$ (XI)

where $R^{68}$ is as defined in relation to formula (X), in the presence of diphenylphosphorylazide. The reaction is suitably effected in an organic solvent such as DMF or DCM at elevated temperatures, for example of from 80 to 120° C.

Compounds of formula (X) may be obtained by deesterification of compounds of formula (XII)

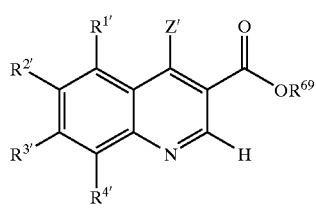

(XII)

where $R^{1'}$, $R^{21}$, $R^{3'}$ $R^{4'}$ and $Z'$ are as defined in relation to formula (III) and $R^{68}$ is a $C_{1-4}$alkyl group such as ethyl. Deesterification is effected by alkaline hydrolysis of the compound of formula (XII) for example using sodium hydroxide as illustrated hereinafter.

Compounds of formula (XII) are known compounds (see for example WO 98343960, U.S. Pat. No. 5,318,963 and EP-A-304158) or they can be obtained from known compounds by analogous methods.

Compounds of the invention are useful in the inhibition of MEK enzyme activity and can be used in the treatment of proliferative disease. They will suitably be in the form of a pharmaceutical composition, in combination with a pharmaceutically acceptable carrier. Such compositions form a further aspect of the invention.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile, aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as absorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, and esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspensions, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, $30\mu$ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of MEK enzymes.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

In a further aspect, the invention provides a method of treating proliferative disease by administering a compound of formula (I), a preferably a compound of formula (IA) as described above, or a pharmaceutical composition as described above.

Yet a further aspect of the invention provides the use of a compound of formula (I) as defined above, in the preparation of a medicament for use in the inhibition of MEK enzyme activity and in particular for the treatment of proliferative disease such as cancer. The invention will now be particularly described by way of Example.

Preparation of 4-chloro-6,7-dimethoxy-3-fluoro-quinoline.

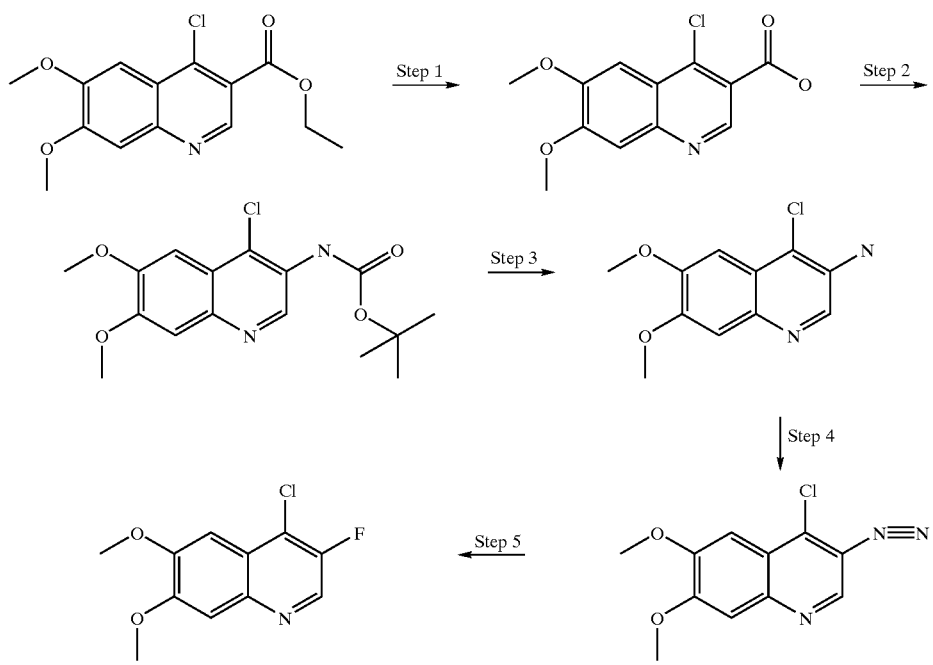

Step 1

4-chloro-6,7-dimethoxy-3-quinolinecarboxylic ethyl ester (ex RSL) (50 g) was suspended in ethanol (400 ml) and aqueous 2M sodium hydroxide (400 ml) was added with stirring, stirred for 24 hours. The reaction mixture was diluted with water (400 ml), cooled in an ice/water bath and brought to pH4 by carefully addition of concentrated hydrochloric acid. The resulting solid was filtered off, washed with water and dried in a vacuum oven at 50° C. To give 4-chloro-6,7-dimethoxy-3-quinolinecarboxylic acid (52.7 g, 98.7%).

Mass Spectrum m/e 268 ($M^+$+H).

NMR Spectrum (d-6-DMSO, δ values) 4.0 (s, 6H), 7.45 (s, 1H), 7.5 (s, 1H), 8.95 (s, 1H).

Step 2

4-chloro-6,7-dimethoxy-3-quinolinecarboxylic acid (26 g) was suspended in DMF (1000 ml) with stirring under a nitrogen atmosphere, tBuOH (400 ml) was added followed by triethylamine (31 ml) and finally Diphenylphosphoryl azide (25 ml) The reaction was then heated to 100° C. for 7 hours with stirring. Cooled and then evaporated on a rotavapor. The residue was treated with dichloromethane, some solid was filtered off, the filtrate was then flash columned (Merck silica Art 9385) eluting with dichloromethane with a methanol gradient to 5%. To give 3-BOCamino-4-chloro-6,7-dimethoxyquinoline (21.6 g, 65%) and 3-amino-4-chloro-6,7-dimethoxyquinoline (4.4 g, 19%).

3-BOCamino-4-chloro-6,7-dimethoxyquinoline

Mass Spectrum m/e 339 ($M^+$+H).

NMR Spectrum (d-6-DMSO, δ values) 1.45 (s, 9H), 3.9 (s, 3H), 3.95 (s, 3H), 7.35 (s, 1H), 7.4 (s, 1H), 8.7 (s, 1H), 9.1 (s, 1H).

Step 3

3-BOCamino-4-chloro-6,7-dimethoxyquinoline (18 g) was dissolved in trifluoroacetic acid (200 ml) with stirring, triethylsilane (80 ml) was then added. Stirred at room temperature for 2 hours. Evaporated. The dark red oily residue was treated with ice/water and carefully basified with 880 ammonia. The resulting red gum was scratched and stirred upon which it slowly solidified. Solid was filtered off and washed with water. Dried to give 3-amino-4-chloro-6, 7-dimethoxyquinoline (7 g). On standing overnight more solid came out of the filtrate this was filtered off washed with water and dried to give 3-amino-4-chloro-6,7-dimethoxyquinoline (3.5 g) (Total yield 83%).

Mass Spectrum m/e 239 ($M^+$+H).

NMR Spectrum (d-6-DMSO, δ values), 3.85 (s, 3H), 3.9 (s, 3H), 5.65 (s, 2H), 7.1 (s, 1H), 7.25 (s, 1H), 8.35 (s, 1H).

Step 4

3-amino-4-chloro-6,7-dimethoxyquinoline (3.3 g) was dissolved in tetrahydrofuran (70 ml) with stirring and then cooled in an ice/water bath to below 10° C. 48% aqueous fluoboric acid (7.3 ml) was then added and the mixture stirred for 5 minutes. A solution of sodium nitrite (1.05 g) in water (2 ml) was added keeping the temperature below 10° C. The reaction mixture was then stirred for 30 minutes with cooling. The resulting yellow solid was filtered off, washed with fresh tetrahydrofuran. Carefully vac dried. To give 4-chloro-6,7-dimethoxyquinoline-3-diazonium tetrafluoroborate (4.15 g, 89%).

Mass Spectrum m/e no mass ion.

NMR Spectrum (d-6-DMSO, δ values), 3.9 (s, 3H), 3.95 (s, 3H), 7.35 (s, 1H), 7.5 (s, 1H), 9.4 (s, 1H).

Step 5

4-chloro-6,7-dimethoxyquinoline-3-diazonium tetrafluoroborate (2.4 g) was carefully heated to 170° C. Spontaneous decomposition then took place. Gas evolution quickly ceased. Reaction was cooled and flash columned eluting with dichloromethane/acetonitrile 95:5 to give 4-chloro-6,7-dimethoxy-3-fluoroquinoline (0.65 g, 38%).

Mass Spectrum m/e 242 ($M^+$+H).

NMR Spectrum (d-6-DMSO, δ values), 3.9 (s, 3H), 3.95 (s, 3H), 7.3 (s, 1H), 7.45 (s, 1H), 8.8 (s, 1H).

EXAMPLE 1

Preparation of Compound 1 in Table 1

A solution of hydrogen chloride in ether (1 molar, 0.34 ml) was added to a mixture of 4-chloro-6,7-dimethoxy-3-fluoro-quinoline (80 mg) and 4-(2-methoxyphenoxy)-aniline (142 mg) in cyclohexanol (3 ml). The mixture was stirred and heated at 110° C. for 18 hours. The mixture was cooled to ambient temperature and then filtered. The crystals were washed with a small volume of diethyl ether and then dried to give 4-(2-methoxyphenoxy)-anilino-3-fluoro-6,7-dimethoxyquinoline (120 mg, 79%).

Mass Spectrum m/e 421 ($M^+$+H).

NMR Spectrum (d-6-DMSO, δ values), 3.7 (s, 3H), 3.9 (s, 3H), 3.95 (s, 3H), 6.85 (m, 2H), 6.95 (m, 1H), 7.05 (m, 1H), 7.2 (m, 4H), 7.5 (s, 1H), 7.95 (s, 1H), 8.85 (d, 1H).

EXAMPLE 2

By an analogous procedure to that described for Example 1 but using an alternative aniline and by carrying out the reaction for 24 hours instead of 18, the following compounds were prepared as summarised in the following Table 2.

TABLE 2

| No. | Starting aniline | Mass spec | n.m.r. |
|---|---|---|---|
| 2 | 2-fluoroaniline | m/e 317 ($M^+$ + H). | (d-6-DMSO, δ values), 3.95(s, 3H), 3.98(s, 3H), 7.25(m, 1H), 7.35(m, 2H), 7.5(m, 2H), 8.1(s, 1H), 8.9(d, 1H), 10.5(broad, 1H). |
| 3 | 4-chloro-2-fluoro-aniline | m/e 351 ($M^+$ + H). | (d-6-DMSO, δ values), 3.95(s, 3H), 4.0(s, 3H), 7.4(d, 1H), 7.6(m, 3H), 8.1(s, 1H), 8.9 (d, 1H). |
| 4 | 3,4-dichloroaniline) | m/e 367 ($M^+$ + H). | (d-6-DMSO, δ values), 3.95(s, 3H), 3.98(s, 3H), 7.3(m, 1H), 7.5(s, 1H), 7.55(m, 1H), 7.6(d, 1H), 8.0(s, 1H), 8.95(d, 1H), 10.56 (broad, 1H). |
| 5 | 4-phenoxyaniline | m/e 391 ($M^+$ + H). | (d-6-DMSO, δ values), 3.95(s, 6H), 7.05(m, 4H), 7.15(m, 1H), 7.35(m, 4H), 7.5(s, 1H), 8.0(s, 1H), 8.9(d, 1H). |
| 6 | [structure] | m/e 434 ($M^+$ + H). | (d-6-DMSO, δ values), 1.15(t, 3H), 3.1(q, 2H), 3.95(s, 3H), 3.98(s, 3H), 6.6(m, 1H), 6.75(s, 1H), 6.95(m, 1H), 7.1(m, 2H), 7.3 (m, 1H), 7.35(m, 2H), 7.5(s, 1H), 8.1(s, 1H), 8.9(d, 1H), 10.65(broad, 1H). |
| 7 | [structure] | m/e 409 ($M^+$ + H). | (d-6-DMSO, δ values), 3.95(s, 3H), 3.98(s, 3H), 7.0(m, 2H), 7.2(m, 3H), 7.35(m, 3H), 7.5(s, 1H), 8.0(s, 1H), 8.9(d, 1H), 10.48 (broad, 1H). |
| 8 | [structure] | m/e 409 ($M^+$ + H). | (d-6-DMSO, δ values), 3.75(s, 3H), 3.95(s, 3H), 3.98(s, 3H), 6.7(m, 2H), 6.8(d, 1H), 7.1(d, 1H), 7.3(t, 1H), 7.5(s, 1H), 7.85(m, 1H), 8.1(s, 1H), 8.2(s, 1H), 8.9(d, 1H), 10.6(broad, 1H). |
| 9 | [structure] | m/e 398 ($M^+$ + H). | (d-6-DMSO, δ values), 3.85(s, 3H), 3.9(s, 3H), 6.95(m, 2H), 7.15(d, 1H), 7.25(m, 3H), 7.35(s, 1H), 7.45(s, 1H), 8.5(d, 1H), 8.75(s, 1H). |

TABLE 2-continued

| No. | Starting aniline | Mass spec | n.m.r |
|---|---|---|---|
| 10 | 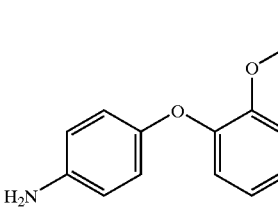 | m/e 435 (M⁺ + H). | (d-6-DMSO, δ values), 1.15(t, 3H), 3.95(s, 3H), 3.98(s, 3H), 4.0(q, 2H), 6.9(m, 2H), 6.95(m, 1H), 7.05(m, 1H), 7.15(m, 2H), 7.25(m, 2H), 7.45(s, 1H), 7.95(s, 1H), 8.85 (d, 1H), 10.35(s, 1H). |
| 11 | 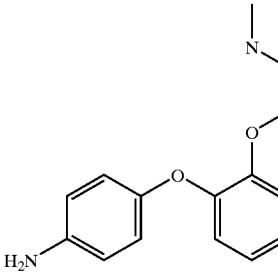 | m/e 478 (M⁺ + H). | (d-6-DMSO, δ values), 2.6(d, 3H), 3.85(s, 3H), 3.9(s, 3H), 4.45(s, 2H), 6.9(m, 2H), 7.0(m, 6H), 7.3(s, 1H), 7.4(broad, 1H), 7.6 (s, 1H), 8.55(d, 1H), 9.0(broad, 1H). |
| 12 | 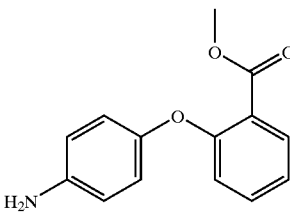 | m/e 449 (M⁺ + H). | (d-6-DMSO, δ values), 3.7(s, 3H), 3.95(s, 3H), 3.98(s, 3H), 6.95(m, 2H), 7.05.(d, 1H), 7.3(m, 3H), 7.45(s, 1H), 7.6(m, 1H), 7.85 (d, 1H), 7.95(s, 1H), 8.9(d, 1H), 10.38 (broad, 1H). |
| 13 | 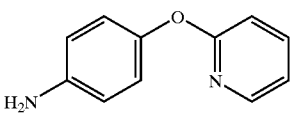 | m/e 329 (M⁺ + H). | (d-6-DMSO, δ values), 3.95(s, 3H), 3.98(s, 3H), 6.95(,m, 2H) 7.05(d, 1H) 7.15(m, 3H), 7.35(m, 2H) 7.5(s, 1H), 7.85(m, 1H), 8.0(s, 1H), 8.15(m, 1H), 8.9(d, 1H), 10.52 (broad, 1H). |
| 14 | 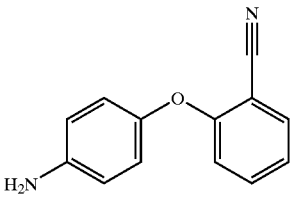 | m/e 416 (M⁺ + H). | (d-6 DMSO, δvalues), 3.95(s, 6H), 6.95(d, 1H), 7.2(d 2H), 7.3(t, 1H), 7.4(m, 2H), 7.5(s, 1H), 7.7(m, 1H), 7.9(m, 1H), 8.05(s, 1H), 8.9(d, 1H), 10.49(broad, 1H). |
| 15 | 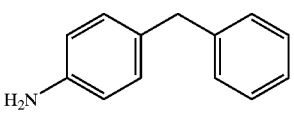 | m/e 389 (M⁺ + H). | (d-6-DMSO, δ values), 3.85(s, 3H), 3.9(s, 3H), 3.95(s, 2H), 7.2(m, 9H), 7.5(s, 1H), 7.9(s, 1H), 8.9(d, 1H), 10.39(broad, 1H). |
| 16 | 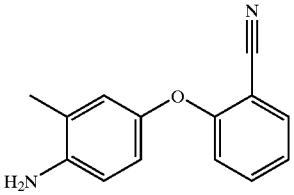 | m/e 430 (M⁺ + H). | (d-6-DMSO, δ values), 2.25(s, 3H), 3.85(s, 3H), 3.9(s, 3H), 6.9(m, 2H), 7.0(m, 2H) 7.25(m, 2H), 7.5(s, 1H), 7.65(t, 1H), 7.85 (d, 1H) 8.05(s, 1H), 8.4(d, 1H) |
| 17 | 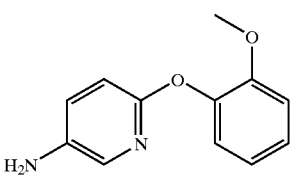 | m/e 422 (M⁺ + H). | (d-6-DMSO, δ values), 3.7(s, 3H), 3.85(s, 3H), 3.88(s, 3H), 6.85(d, 1H), 6.9(m, 1H), 7.1(m, 3H), 7.3(s, 1H), 7.4(m, 1H), 7.5(s, 1H), 7.8(m, 1H), 8.45(d, 1H), 8.55(s, 1H) |

TABLE 2-continued

| No. | Starting aniline | Mass spec | n.m.r. |
|---|---|---|---|
| 18 | 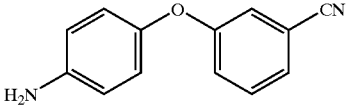 | m/e 416 (M⁺ + H). | (d-6-DMSO, δ values), 3.85(s, 3H), 3.9(s, 3H), 7.0(m, 4H), 7.3(m, 1H), 7.35(m, 2H), 7.5(m, 3H), 8.5(d, 1H), 8.65(s, 1H) |

Biological Results
Assay for inhibitors of the MAP kinase pathway

To evaluate inhibitors of the MAPK pathway a coupled assay was carried out which measures phosphorylation of serine/threonine residues present in the substrate in the presence or absence of inhibitor. Recombinant glutathione S-transferase fusion protein containing human p45MEK1 (GST-MEK) was activated by c-raf (Sf9 insect cell lysate from triple baculoviral infection with c-raf/ras/lck) and used for the assay. Active GST-MEK was first used to activate a recombinant glutathione S-transferase fusion protein containing p44MAP kinase (GST-MAPK) in the presence of ATP and $Mg^{2+}$ for 60 min at room temperature in the presence or absence of potential inhibitors. The activated GST-MAPK was then incubated with myelin basic protein (MBP) as substrate for 10 min at room temperature in the presence of ATP, $Mg^{2+}$ and $^{33}$P-ATP. The reaction was stropped by addition of 20% v/v phosphoric acid. Incorporation of $^{33}$P into the myelin basic protein was determined by capture of the substrate on a filter mat, washing and counting using scintillation methods. The extent of inhibition was determined by comparison with untreated controls.

The final assay solution contained 10 mM Tris, pH 7.5, 0.05 mM EGTA, 8.33 μM [γ$^{33}$P]ATP, 8.33 mM Mg(OAc)$_2$, 0.5 mM sodium orthovanadate, 0.05% w/v BSA, 6.5 ng GST-MEK, 1 μg GST-MAPK and 16.5 μg MBP in a reaction volume of 60 μl.

Compounds tested of the present invention had $IC_{50}$ results typically less than 20 μM. For example, Compound No 5 of Example 2 gave an $IC_{50}$ of 0.55 μM.

In vitro MAP kinase assay

To determine whether compounds were inhibiting GST-MEK or GST-MAPK, a direct assay of MAPK activity was employed. GST-MAPK was activated by a constitutively active GST-MEK fusion protein containing two point mutations (S217E, S221E) and used for the assay in the presence and absence of potential inhibitors. The activated GST-MAPK was incubated with substrate (MBP) for 60 min at room temperature in the presence of ATP, $Mg^{2+}$ and $^{33}$P-ATP. The reaction was stopped by addition of 20% v/v phosphoric acid. Incorporation of $^{33}$P into the myelin basic protein was determined by capture of the substrate on a filter mat, washing and counting using scintillation methods.

The final assay solution contained 12 mM Tris, pH 7.5, 0.06 mM EGTA, 30 μM [γ$^{33}$P]ATP, 10 mM Mg(OAc)$_2$, 0.6 mM sodium orthovanadate, 0.06% w/v BSA, 28 ng GST-MAPK and 16.5 μg MBP in a reaction volume of 60 μl.

Compounds of the invention showed activity in this screen.

Cell proliferation assays

Cells were seeded into multi-well plates at 20,000–40,000 cells/ml in growth medium containing 5% FCS and incubated overnight at 37° C. The compounds were prepared in fresh medium at an appropriate concentration and added to the wells containing the cells. These were then incubated for a further 72 hours. Cells were then either removed from the wells by incubating with trypsin/EDTA and counted using a Coulter counter, or treated with XTT/PMS in PBSA and optical densities read at 450 nM. Compounds tested of the present invention had $IC_{50}$ results typically less then 30 μM. For example, Compound No 4 of Example 2 gave an IC50 of 3.8 μM in HT29 human colon tumour cells.

What is claimed is:

1. A compound of formula (IA)

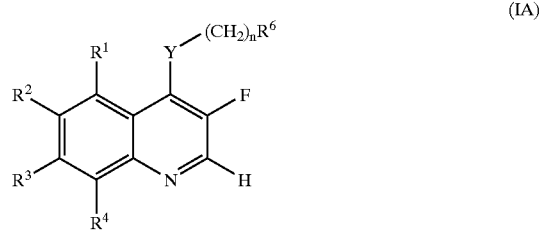

(IA)

or a pharmaceutically acceptable salt thereof, wherein:

n is 0–1;

Y is selected from —NH—, —O—, —S—, or —NR$^7$— where R$^7$ is alkyl of 1–6 carbon atoms;

R$^6$ is cycloalkyl of 3 to 7 carbon atoms, which may be optionally substituted with one or more alkyl of 1 to 6 carbon atom groups; or is a pyridinyl, pyrimidinyl, or phenyl ring with one, two or three substituent groups wherein each substituent group is selected from the group consisting of alkyl of 4–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 4–6 carbon atoms, alkylthio of 1–6 carbon atoms, nitro, carboxy, carboalkoxy of 2–7 carbon atoms, carboalkyl of 2–7 carbon atoms, phenoxy, phenyl, benzoyl, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino;

or R$^6$ is a group —R$^8$—X—R$^9$ where

R$^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;

X is selected from $CH_2$, —NH—, —O—, —S—, or —$NR^5$— where $R^5$ is alkyl of 1–6 carbon atoms, and $R^9$ is a group $(CH_2)_m R^{10}$ where m is 0, or an integer of from 1–3 and $R^{10}$ is an optionally substituted aryl or optionally substituted cycloalkyl ring of up to 10 carbon atoms, or $R^{10}$ is a heterocyclic ring containing 1 or 2 oxygen atoms and optionally one or more substituents;

$R^1$, $R^2$, $R^3$ and $R^4$ are each independently selected from hydrogen, hydroxy, halogeno, cyano, nitro, trifluoromethyl, $C_{1-3}$alkyl, —$NR^{11}R^{12}$ (wherein $R^{11}$ and $R^{12}$, which may be the same or different, each represents hydrogen or $C_{1-3}$alkyl), or a group $R^{13}$—$X^1$—$(CH_2)_x$ wherein x is 0 to 3, $X^1$ represents —O—, —$CH_2$—, —OCO—, carbonyl, —S—, —SO—, —$SO_2$—, —$NR^{14}CO$—, —$CONR^{15}$—, —$SO_2NR^{16}$—, —$NR^{17}SO_2$— or —$NR^{18}$— (wherein $R^{14}$, $R^{15}$, $R^{16}$, $R^{17}$ and $R^{18}$ each independently represents hydrogen, $C_{1-3}$alkyl or $C_{1-3}$alkoxy$C_{2-3}$alkyl) and $R^{13}$ is selected from one of the following sixteen groups:

1) $C_{1-5}$alkyl which may be unsubstituted or which may be substituted with one or more groups selected from hydroxy, fluoro and amino;
2) $C_{1-5}$alkyl$X^2COR^{19}$ (wherein $X^2$ represents —O— or —$NR^{20}$— (wherein $R^{20}$ represents hydrogen, $C_{1-3}$alkyl or $C_{1-3}$alkoxy$C_{2-3}$alkyl) and $R^{19}$ represents —$NR^{21}R^{22}$— or —$OR^{23}$— (wherein $R^{21}$, $R^{22}$ and $R^{23}$ which may be the same or different each represents hydrogen, $C_{1-3}$alkyl or $C_{1-3}$alkoxy$C_{2-3}$alkyl));
3) $C_{1-5}$alkyl$X^3R^{24}$ (wherein $X^3$ represents —O—, —S—, —SO—, —$SO_2$—, —OCO—, —$NR^{25}CO$—, —$CONR^{26}$—, —$SO_2NR^{27}$—, —$NR^{28}SO_2$— or —$NR^{29}$— (wherein $R^{25}$, $R^{26}$, $R^{27}$, $R^{28}$ and $R^{29}$ each independently represents hydrogen, $C_{1-3}$alkyl or $C_{1-3}$alkoxy$C_{2-3}$alkyl) and $R^{24}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);
4) $C_{1-5}$alkyl$X^4C_{1-5}$alkyl$X^5R^{30}$ (wherein $X^4$ and $X^5$ which may be the same or different are each —O—, —S—, —SO—, —$SO_2$—, —$NR^{31}CO$—, —$CONR^{32}$—, —$SO_2NR^{33}$—, —$NR^{34}SO_2$— or —$NR^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);
5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);
6) $(CH_2)_q X^6 R^{37}$ (wherein q is an integer from 0 to 5, $X^6$ represents a direct bond, —O—, —S—, —SO—, —$SO_2$—, —$NR^{38}CO$—, —$CONR^{39}$—, —$SO_2NR^{40}$—, —$NR^{41}SO_2$— or —$NR^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —$CONR^{43}R^{44}$ and —$NR^{45}COR^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));
7) $C_{2-6}$alkenyl$R^{36}$ (wherein $R^{36}$ is as defined hereinbefore);
8) $C_{2-6}$alkynyl$R^{36}$ (wherein $R^{36}$ is as defined hereinbefore);
9) $X^7R^{47}$ (wherein $X^7$ is —$SO_2$—, —O— or —$CONR^{48}R^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is —$SO_2$—, $X^1$ is —O—, when $X^7$ is —O—, $X^1$ is carbonyl, when $X^7$ is —$CONR^{48}R^{49}$—, $X^1$ is —O— or $NR^{18}$ (wherein $R^{48}$, $R^{49}$ and $R^{18}$ are as defined hereinbefore);
10) $C_{2-6}$alkenyl$R^{37}$ (wherein $R^{37}$ is as defined hereinbefore);
11) $C_{2-6}$alkynyl$R^{37}$ (wherein $R^{37}$ is as defined hereinbefore);
12) $C_{2-6}$alkenyl$X^8R^{37}$ (wherein $X^8$ represents —O—, —S—, —SO—, —$SO_2$—, —$NR^{50}CO$—, —$CONR^{51}$—, —$SO_2NR^{52}$—, —$NR^{53}SO_2$— or —$NR^{54}$— (wherein $R^{50}$, $R^{51}$, $R^{52}$, $R^{53}$ and $R^{54}$ each independently represents hydrogen, $C_{1-3}$alkyl or $C_{1-3}$alkoxy$C_{2-3}$alkyl) and $R^{37}$ is as defined hereinbefore);
13) $C_{2-6}$alkynyl$X^9R^{37}$ (wherein $X^9$ represents —O—, —S—, —SO—, —$SO_2$—, —$NR^{55}CO$—, —$CONR^{56}$—, —$SO_2NR^{57}$—, —$NR^{58}SO_2$— or —$NR^{59}$— (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R^{37}$ is as defined hereinbefore);
14) $C_{1-3}$alkyl$X^{10}C_{1-3}$alkyl$R^{37}$ (wherein $X^{10}$ represents —O—, —S—, —SO—, —$SO_2$—, —$NR^{60}CO$—, —$CONR^{61}$—, —$SO_2NR^{62}$—, —$NR^{63}SO_2$— or —$NR^{64}$— (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);
15) $R^{36}$ (wherein $R^{36}$ is as defined hereinbefore); and
16) $C_{1-3}$alkyl$X^{10}C_{1-3}$alkyl$R^{36}$ (wherein $X^{10}$ and $R^{36}$ are as defined hereinbefore).

2. A compound according to claim 1 wherein $R^6$ is a group —$R^8$—X—$R^9$ where $R^8$, $R^9$ and X are as defined in claim 1.

3. A compound according to claim 2 wherein $R^{10}$ is an aryl, carbocyclic or heterocyclic group substituted by one or more groups selected from hydroxy; halo; nitro; cyano; carboxy; $C_{1-6}$alkoxy; $C_{1-6}$alkyl; $C_{2-6}$alkenyl; $C_{2-6}$alkynyl; $C_{2-6}$alkenyloxy; $C_{2-6}$alkynyloxy; $C_{3-6}$cycloalkyl; amino;

mono- or di-C$_{1-6}$alkyl amino; heterocyclyl optionally substituted with C$_{1-6}$alkyl or oxo; C(O)R$^a$; C(O)OR$^a$; S(O)$_d$R$^a$; NR$^a$C(O)R$^b$; C(O)NR$^a$S(O)$_d$R$^b$; C(O)NR$^a$R$^b$; NR$^a$C(O)NR$^b$R$^c$; NR$^a$S(O)$_d$R$^b$ or N(S(O)$_d$R$^b$)S(O)$_d$R$^c$ where d is 0, 1 or 2 and R$^a$, R$^b$ and R$^c$ are independently selected from hydrogen, C$_{1-6}$alkyl, aryl, C$_{3-6}$cycloalkyl or heterocylcyl, and wherein any alkyl, alkenyl or alkynyl group or moiety contained within the substituent R$^{10}$ may themselves be optionally substituted with one or more groups selected from hydroxy; cyano; nitro; halo; carboxy; carboalkoxy of 2–7 carbon atoms; C$_{3-6}$cycloalkyl; heterocyclyl optionally substituted with C$_{1-6}$alkyl or oxo; C(O)R$^d$; C(O)OR$^d$; NR$^d$R$^e$; S(O)$_e$R$^d$; NR$^d$C(O)R$^e$; C(O)NR$^d$R$^e$; NR$^d$C(O)NR$^e$R$^f$; NR$^d$S(O)$_e$R$^e$ where e is 0, 1 or 2 and R$^d$, R$^e$ and R$^f$ are independently selected from hydrogen or C$_{1-6}$alkyl optionally substituted with one or more groups selected from hydroxy; cyano; nitro; halo; carboxy; carboalkoxy of 2–7 carbon atoms; C$_{3-6}$cycloalkyl; heterocyclyl optionally substituted with C$_{1-6}$alkyl or oxo; C(O)R$^g$; C(O)OR$^g$; NR$^g$R$^h$; S(O)$_e$R$^g$; NR$^h$C(O)R$^g$; C(O)NR$^g$R$^h$; NR$^g$C(O)NR$^h$R$^i$; NR$^g$S(O)$_e$R$^h$ where e is as defined above and R$^g$, R$^h$ and R$^i$ are independently selected from hydrogen or C$_{1-6}$alkyl; or two substituents on adjacent atoms may be joined to form the second ring of a bicyclic ring system wherein the said second ring is optionally substituted with one or more of the groups listed above for R$^9$ and optionally contains one or more heteroatoms.

4. A compound according to claim 3 wherein R$^{10}$ is phenyl substituted by an optionally substituted alkoxy group.

5. A compound of formula (IB)

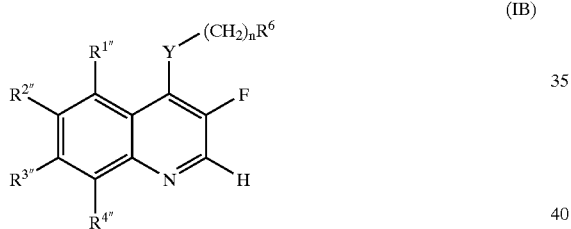

(IB)

or a pharmaceutically acceptable salt thereof
wherein
n is 0–1;
Y is selected from —NH—, —O—, —S—, or —NR$^7$— where R$^7$ is alkyl of 1–6 carbon atoms;
R$^6$ is cycloalkyl of 3 to 7 carbon atoms, which may be optionally substituted with one or more alkyl of 1 to 6 carbon atom groups; or is a pyridinyl, pyrimidinyl, or phenyl ring;
wherein the pyridinyl, pyrimidinyl, or phenyl ring may be substituted with one, two or three groups selected from the group consisting of halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, benzoyl, amino, alkylamino of 1–6 carbon atoms, dialkylamino of 2 to 12 carbon atoms, alkanoylamino of 1–6 carbon atoms, alkenoylamino of 3–8 carbon atoms, alkynoylamino of 3–8 carbon atoms, and benzoylamino;

or R$^6$ is a group —R$^8$—X—R$^9$ where
R$^8$ is a divalent cycloalkyl of 3 to 7 carbon atoms, which may be optionally further substituted with one or more alkyl of 1 to 6 carbon atom groups; or is a divalent pyridinyl, pyimidinyl, or phenyl ring; wherein the pyridinyl, pyrimidinyl, or phenyl ring may be optionally further substituted with one or more groups selected from halogen, alkyl of 1–6 carbon atoms, alkenyl of 2–6 carbon atoms, alkynyl of 2–6 carbon atoms, azido, hydroxyalkyl of 1–6 carbon atoms, halomethyl, alkoxymethyl of 2–7 carbon atoms, alkanoyloxymethyl of 2–7 carbon atoms, alkoxy of 1–6 carbon atoms, alkylthio of 1–6 carbon atoms, hydroxy, trifluoromethyl, cyano, nitro, carboxy, carboalkoxy of 2–7 carbon atoms, carboalkyl of 2–7 carbon atoms, phenoxy, phenyl, thiophenoxy, benzoyl, benzyl, amino, alkylamino of 1–6 carbon atoms, dialkylamino of 2 to 12 carbon atoms, phenylamino, benzylamino, alkanoylamino of 1–6 carbon atoms, alkenoylamino of 3–8 carbon atoms, alkynoylamino of 3–8 carbon atoms, and benzoylamino;
X is selected from CH$_2$, —NH—, —O—, —S—, or —NR$^5$— where R$^5$ is alkyl of 1–6 carbon atoms, and
R$^9$ is a group (CH$_2$)$_m$R$^{10}$ where m is 0, or an integer of from 1–3 and R$^{10}$ is an optionally substituted aryl or optionally substituted cycloalkyl ring of up to 10 carbon atoms, or R$^{10}$ is a heterocyclic ring containing 1 or 2 oxygen atoms and optionally one or more substituents; and
at least one of R$^{1"}$, R$^{2"}$, R$^{3"}$ or R$^{4"}$ is a group R$^{13'}$—X$^1$—(CH$_2$)$_x$ wherein x and X$^1$ are as defined below and R$^{13'}$ is alkyl substituted by chloro or bromo; and the remainder of the groups R$^{1"}$, R$^{2"}$, R$^{3"}$ or R$^{4"}$ are the groups of R$^1$, R$^2$, R$^3$ and R$^4$ respectively where R$^1$, R$^2$, R$^3$ and R$^4$ are each independently selected from hydrogen, hydroxy, halogeno, cyano, nitro, trifluoromethyl, C$_{1-3}$alkyl, —NR$^{11}$R$^{12}$ (wherein R$^{11}$ and R$^{12}$, which may be the same or different, each represents hydrogen or C$_{1-3}$alkyl), or a group R$^{13}$—X$^1$—(CH$_2$)$_x$ wherein x is 0 to 3, X$^1$ represents —O—, —CH$_2$—, —OCO—, carbonyl, —S—, —SO—, —SO$_2$—, —NR$^{14}$CO—, —CONR$^{15}$—, —SO$_2$NR$^{16}$—, —NR$^{17}$SO$_2$— or —NR$^{18}$— (wherein R$^{14}$, R$^{15}$, R$^{16}$, R$^{17}$ and R$^{18}$ each independently represents hydrogen, C$_{1-3}$alkyl or C$_{1-3}$alkoxyC$_{2-3}$alkyl) and R$^{13}$ is selected from one of the following sixteen groups:
1) C$_{1-5}$alkyl which may be unsubstituted or which may be substituted with one or more groups selected from hydroxy, fluoro and amino;
2) C$_{1-5}$alkylX$^2$COR$^{19}$ (wherein X$^2$ represents —O— or —NR$^{20}$— (wherein R$^{20}$ represents hydrogen, C$_{1-3}$alkyl or C$_{1-3}$alkoxyC$_{2-3}$alkyl) and R$^{19}$ represents —NR$^{21}$R$^{22}$— or —OR$^{23}$— (wherein R$^{21}$, R$^{22}$ and R$^{23}$ which may be the same or different each represents hydrogen, C$_{1-3}$alkyl or C$_{1-3}$alkoxyC$_{2-3}$alkyl));
3) C$_{1-5}$alkylX$^3$R$^{24}$ (wherein X$^3$ represents —O—, —S—, —SO—, —SO$_2$—, —OCO—, —NR$^{25}$CO—, —CONR$^{26}$—, —SO$_2$NR$^{27}$—, —NR$^{28}$SO$_2$— or —NR$^{29}$— (wherein R$^{25}$, R$^{26}$, R$^{27}$, R$^{28}$ and R$^{29}$ each independently represents hydrogen, C$_{1-3}$alkyl or C$_{1-3}$alkoxyC$_{2-3}$alkyl) and R$^{24}$ represents hydrogen, C$_{1-3}$alkyl, cyclopentyl, cyclohexyl or a 5 or 6 membered saturated heterocyclic group with one or two heteroatoms, selected independently from O, S and N, which C$_{1-3}$alkyl group may bear one or two substituents selected from oxo, hydroxy, halogeno and $C_{1-4}$alkoxy and which cyclic group may bear one or two substituents selected from oxo, hydroxy, halogeno, $C_{1-4}$alkyl, $C_{1-4}$hydroxyalkyl and $C_{1-4}$alkoxy);

4) $C_{1-5}$alkyl$X^4C_{1-5}$alkyl$X^5R^{30}$ (wherein $X^4$ and $X^5$ which may be the same or different are each —O—, —S—, —SO—, —SO$_2$—, —NR$^{31}$CO—, —CONR$^{32}$—, —SO$_2$NR$^{33}$—, —NR$^{34}$SO$_2$— or —NR$^{35}$— (wherein $R^{31}$, $R^{32}$, $R^{33}$, $R^{34}$ and $R^{35}$ each independently represents hydrogen, $C_{1-3}$alkyl or $C_{1-3}$alkoxy$C_{2-3}$alkyl) and $R^{30}$ represents hydrogen or $C_{1-3}$alkyl);

5) $C_{1-5}$alkyl$R^{36}$ (wherein $R^{36}$ is a 5 or 6 membered saturated heterocyclic group with one or two heteroatoms, selected independently from O, S and N, which heterocyclic group may bear one or two substituents selected from oxo, hydroxy, halogeno, $C_{1-4}$alkyl, $C_{1-4}$hydroxyalkyl and $C_{1-4}$alkoxy);

6) $(CH_2)_qX^6R^{37}$ (wherein q is an integer from 0 to 5, $X^6$ represents a direct bond, —O—, —S—, —SO—, —SO$_2$—, —NR$^{38}$CO—, —CONR$^{39}$—, —SO$_2$NR$^{40}$—, —NR$^{41}$SO$_2$— or —NR$^{42}$— (wherein $R^{38}$, $R^{39}$, $R^{40}$, $R^{41}$ and $R^{42}$ each independently represents hydrogen, $C_{1-3}$alkyl or $C_{1-3}$alkoxy$C_{2-3}$alkyl) and $R^{37}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, amino, $C_{1-4}$alkyl, $C_{1-4}$alkoxy, $C_{1-4}$hydroxyalkyl, $C_{1-4}$hydroxyalkoxy, $C_{1-4}$aminoalkyl, $C_{1-4}$alkylamino, carboxy, cyano, —CONR$^{43}R^{44}$ and —NR$^{45}$COR$^{46}$ (wherein $R^{43}$, $R^{44}$, $R^{45}$ and $R^{46}$, which may be the same or different, each represents hydrogen, $C_{1-4}$alkyl or $C_{1-3}$alkoxy$C_{2-3}$alkyl));

7) $C_{2-6}$alkenyl$R^{36}$ (wherein $R^{36}$ is as defined hereinbefore);

8) $C_{2-6}$alkynyl$R^{36}$ (wherein $R^{36}$ is as defined hereinbefore);

9) $X^7R^{47}$ (wherein $X^7$ is —SO$_2$—, —O— or —CONR$^{48}R^{49}$— (wherein $R^{48}$ and $R^{49}$, which may be the same or different, each represents hydrogen, $C_{1-3}$alkyl or $C_{1-3}$alkoxy$C_{2-3}$alkyl) and $R^{47}$ represents $C_{1-5}$alkyl which may be unsubstituted or which may be substituted with one or more groups selected from hydroxy, fluoro and amino) with the provisos that when $X^7$ is —SO$_2$—, $X^1$ is —O—, when $X^7$ is —O—, $X^1$ is carbonyl, when $X^7$ is —CONR$^{48}R^{49}$—, $X^1$ is —O— or NR$^{18}$ (wherein $R^{48}$, $R^{49}$ and $R^{18}$ are as defined hereinbefore);

10) $C_{2-6}$alkenyl$R^{37}$ (wherein $R^{37}$ is as defined hereinbefore);

11) $C_{2-6}$alkynyl$R^{37}$ (wherein $R^{37}$ is as defined hereinbefore);

12) $C_{2-6}$alkenyl$X^8R^{37}$ (wherein $X^8$ represents —O—, —S—, —SO—, —SO$_2$—, —NR$^{50}$CO—, —CONR$^{51}$—, —SO$_2$NR$^{52}$—, —NR$^{53}$SO$_2$— or —NR$^{54}$— (wherein $R^{50}$, $R^{51}$, $R^{52}$, $R^{53}$ and $R^{54}$ each independently represents hydrogen, $C_{1-3}$alkyl or $C_{1-3}$alkoxy$C_{2-3}$alkyl) and $R^{37}$ is as defined hereinbefore);

13) $C_{2-6}$alkynyl$X^9R^{37}$ (wherein $X^9$ represents —O—, —S—, —SO—, —SO$_2$—, —NR$^{55}$CO—, —CONR$^{56}$—, —SO$_2$NR$^{57}$—, —NR$^{58}$SO$_2$— or —NR$^{59}$— (wherein $R^{55}$, $R^{56}$, $R^{57}$, $R^{58}$ and $R^{59}$ each independently represents hydrogen, $C_{1-3}$alkyl or $C_{1-3}$alkoxy$C_{2-3}$alkyl) and $R^{37}$ is as defined hereinbefore);

14) $C_{1-3}$alkyl$X^{10}C_{1-3}$alkyl$R^{37}$ (wherein $X^{10}$ represents —O—, —S—, —SO—, —SO$_2$—, —NR$^{60}$CO—, —CONR$^{61}$—, —SO$_2$NR$^{62}$—, —NR$^{63}$SO$_2$— or —NR$^{64}$— (wherein $R^{60}$, $R^{61}$, $R^{62}$, $R^{63}$ and $R^{64}$ each independently represents hydrogen, $C_{1-3}$alkyl or $C_{1-3}$alkoxy$C_{2-3}$alkyl) and $R^{37}$ is as defined hereinbefore);

15) $R^{36}$ (wherein $R^{36}$ is as defined hereinbefore); and

16) $C_{1-3}$alkyl$X^{10}C_{1-3}$alkyl$R^{36}$ (wherein $X^{10}$ and $R^{36}$ are as defined hereinbefore).

6. A pharmaceutical composition comprising a compound of formula (IA) as defined in claim 1 in combination with a pharmaceutically acceptable carrier or excipient.

7. A process for preparing a compound of formula (IA) as defined in claim 1 which method comprises reacting a compound of formula (III)

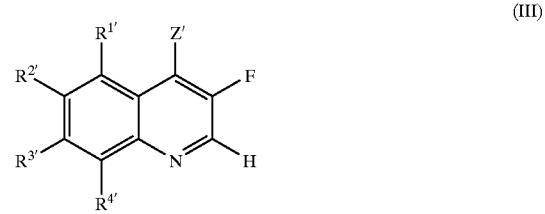

(III)

where $R^{1'}$, $R^{2'}$, $R^{3'}$, $R^{4'}$ represent $R^1$, $R^2$, $R^3$ and $R^4$ respectively as defined in relation to formula (IA) or a precursor thereof, and Z' is a leaving group, with a compound of formula (IV)

(IV)

wherein Y, X, and n are as defined in relation to formula (IA), and $R^{6'}$ is a group $R^6$ as defined in relation to formula (IA) or a precursor thereof; and thereafter if necessary or desired converting precursor groups $R^{1'}$, $R^{2'}$, $R^{3'}$, $R^{4'}$ and $R^{6'}$ to groups of formula $R^1$, $R^2$, $R^3$, $R^4$ and $R^6$ respectively, or converting a group $R^1$, $R^2$, $R^3$, $R^4$ and $R^6$ to a different such group.

8. A method of treating a disease or medical condition mediated by the inhibition of MEK enzyme activity which comprises administering to a mammal in need thereof an inhibition-effective amount of a compound of formula (IA) as defined in claim 1.

* * * * *